(12) United States Patent
Hagiwara et al.

(10) Patent No.: US 9,873,920 B2
(45) Date of Patent: Jan. 23, 2018

(54) METHOD FOR EVALUATING SIDE-EFFECT ONSET RISK IN ANTICANCER DRUG TREATMENT, INCLUDING DETECTING MUC4 GENE POLYMORPHISM

(71) Applicant: SAITAMA MEDICAL UNIVERSITY, Saitama (JP)

(72) Inventors: Koichi Hagiwara, Saitama (JP); Hitoshi Miyazawa, Saitama (JP); Jun Shiihara, Saitama (JP); Tomoaki Tanaka, Saitama (JP); Yoshiaki Inoue, Saitama (JP)

(73) Assignee: SAITAMA MEDICAL UNIVERSITY, Saitama (JP)

( * ) Notice: Subject to any disclaimer, the term of this patent is extended or adjusted under 35 U.S.C. 154(b) by 0 days.

(21) Appl. No.: 14/771,465

(22) PCT Filed: Feb. 27, 2014

(86) PCT No.: PCT/JP2014/054796
§ 371 (c)(1),
(2) Date: Aug. 28, 2015

(87) PCT Pub. No.: WO2014/133055
PCT Pub. Date: Sep. 4, 2014

(65) Prior Publication Data
US 2016/0002734 A1 Jan. 7, 2016

(30) Foreign Application Priority Data

Mar. 1, 2013 (JP) ................................. 2013-041305

(51) Int. Cl.
| | | |
|---|---|---|
| *C12Q 1/68* | (2006.01) | |
| *A61K 31/5377* | (2006.01) | |
| *A61K 31/519* | (2006.01) | |
| *A61K 31/4545* | (2006.01) | |
| *A61K 31/7068* | (2006.01) | |
| *A61K 31/4745* | (2006.01) | |
| *A61K 31/337* | (2006.01) | |
| *A61K 31/517* | (2006.01) | |

(52) U.S. Cl.
CPC .......... *C12Q 1/6886* (2013.01); *A61K 31/337* (2013.01); *A61K 31/4545* (2013.01); *A61K 31/4745* (2013.01); *A61K 31/517* (2013.01); *A61K 31/519* (2013.01); *A61K 31/5377* (2013.01); *A61K 31/7068* (2013.01); *C12Q 2600/106* (2013.01); *C12Q 2600/142* (2013.01); *C12Q 2600/156* (2013.01)

(58) Field of Classification Search
CPC ............ C12Q 1/6886; C12Q 2600/156; C12Q 2600/106; A61K 31/337; A61K 31/5377; A61K 31/517; A61K 31/4545; A61K 31/7068; A61K 31/4745; A61K 31/519

USPC ........ 514/49, 234.8, 265.1, 266.4, 283, 318, 514/449; 435/6.11
See application file for complete search history.

(56) References Cited

U.S. PATENT DOCUMENTS

| | | | |
|---|---|---|---|
| 2004/0203144 A1 | 10/2004 | Szymkowski | ................ 435/375 |
| 2012/0128676 A1 | 5/2012 | Goletz et al. | .............. 424/137.1 |
| 2013/0085081 A1 | 4/2013 | Koizumi et al. | .................. 506/9 |

FOREIGN PATENT DOCUMENTS

| | | | | |
|---|---|---|---|---|
| WO | WO 00/60117 A2 | 10/2000 | ............... | C12Q 1/68 |
| WO | WO 2012/170470 A1 | 12/2012 | ............. | C07K 16/28 |

OTHER PUBLICATIONS

Dimopoulou et al. Pulmonary toxicity from novel antineoplastic agents. Annals of Oncology 17: 372-379, 2006. Published online Nov. 16, 2005.*
Price-Schiavi et al. RAT MUC4 (Sialomucin Complex) Reduces Binding of Anti-ERBB2 Antibodies to Tumor Cell Surfaces, A Potential Mechanism for Herceptin Resistance. Int. J. Cancer: 99, 783-791 (2002).*
NCBI Muc4 https://www.ncbi.nlm.nih.gov/gquery/?term=Muc4+homo, accessed on Nov. 14, 2016.*
Chin. J. Lab. Med., (2009). 32:(2)187-189.
"Correspondence." *Am J Respir Crit Care Med.* vol. 177(12), pp. 1397-1398 (2008).
Debailleul et al. (1998). "Human mucin genes MUC2, MUC3, MUC4, MUC5AC, MUC5B, and MUC6 express stable and extremely large mRNAs and exhibit a variable length polymorphism." *The Journal of Biological Chemistry.* 273:(2)881-890.
Hagiwara (2012). Genetic studies for the drug-induced interstitial lung disease and the acute exacerbation of idiopathic pulmonary fibrosis, *Grants-in-Aid for Scientific Research (Kagaku Kenkyuhi Hojokin) Kenkyu Seika Hokokusho.*
Hagiwara (2012). Tokuhatsusei hai sen'isho kyusei zoaku oyobi yakuzaisei hai shogai ni kan'yo suru nipponjin tokuiteki iden soin ni kansuru kenkyu, Heisei 23 Nendo Sokatsu Kenkyu Hokokusho. pp. 3-8, 15-17, 19-21.
Koscinski et al. (2006) "MUC4 gene polymorphism and expression in women with implantation failure." *Human Reproduction.* 21 : (9)2238-2245.
Zhang et al. (2013) "Genetic variants in MUC4 gene are associated with lung cancer risk in a Chinese population." *PLOS ONE* 8:(10)e77723.

(Continued)

*Primary Examiner* — Yih-Horng Shiao
(74) *Attorney, Agent, or Firm* — Harness, Dickey & Pierce, P.L.C.

(57) ABSTRACT

The purpose of the present invention is to provide an evaluation method kit for evaluating the risk of onset of diffuse alveolar damage due to such factors as anticancer drug administration. The purpose of the present invention is also to provide a method for evaluating the risk of onset of side effects in anticancer drug treatment. An evaluation method and evaluation kit for evaluating the risk of onset of diffuse alveolar damage, including detecting gene polymorphism present in the MUC4 gene. A method for evaluating the risk of onset of side effect in anticancer drug treatment, including detecting gene polymorphism present in the MUC4 gene of a patient scheduled for anticancer drug administration.

8 Claims, 5 Drawing Sheets

(56) References Cited

OTHER PUBLICATIONS

International Search Report (ISR) dated May 27, 2014 in PCT/JP2014/054796 with English Translation.
Moniaux, N., et al. (2000) "Alternative splicing generates a family of putative secreted and membrane-associated MUC4 mucins." *Eur. J. Biochem.*, 267:4536-4544.
Chinese Office Action dated Apr. 27, 2016 issued in Chinese Patent Application No. 201480011722.5, with English Translation.
Choudhury, A., et al. (2000) "Human MUC4 Mucin cDNA and its Variants in Pancreatic Carcinoma[1]," *J. Biochem.*, 128:233-243 (Aug. 1, 2000) (XP009044442).
Hubalek, M., et al. (2010) "Resistance to HER2-targeted therapy: mechanisms of trastuzumab resistance and possible strategies to overcome unresponsiveness to treatment." *Wien. Med. Wochenschr.*, vol. 160(19-20):506-512 (Oct. 26, 2010) (XP019862489).
Nollet, S., et al. (1998) "Human mucin gene MUC4: Organization of its 5'-region and polymorphism of its central tandem repeat array." *Biochem. J.*, 332:739-748 (Jun. 15, 1998) (XP55284801).
Extended European Search Report, dated Jul. 11, 2016 issued in the corresponding European Patent Application No. 14756429.8.

\* cited by examiner

METHOD FOR EVALUATING SIDE-EFFECT ONSET RISK IN ANTICANCER DRUG TREATMENT, INCLUDING DETECTING MUC4 GENE POLYMORPHISM

CROSS-REFERENCE TO RELATED APPLICATIONS

This application is a national phase application of PCT Application No. PCT/JP2014/054796, filed on 27 Feb. 2014, which claims benefit of Japanese Patent Application 2013-041305, filed on 1 Mar. 2013. The entire disclosure of the application identified in this paragraph is incorporated herein by reference.

REFERENCE TO A SEQUENCE LISTING

Applicant hereby submits, in compliance with sequence rules 37 C.F.R. §§1.821-1.825, the required Sequence Listing. A copy of the Sequence Listing is being submitted in computer readable format as required by 37 C.F.R. §1.182(e).

This application contains references to amino acid sequences and/or nucleic acid sequences which are being submitted concurrently herewith as the sequence listing text file 61572648_1.TXT file size 68.8 KiloBytes (KB), created on 1 Mar. 2013. The aforementioned sequence listing is hereby incorporated by reference in its entirety.

TECHNICAL FIELD

The present invention relates to: (1) a method for determining the risk of development of diffuse alveolar damage, which method includes detecting an MUC4 gene polymorphism(s); (2) a method for determining the risk of occurrence of a side effect in an anticancer drug therapy, which method includes detecting an MUC4 gene polymorphism(s); (3) a kit used for these purposes; and the like.

BACKGROUND

Administration of an anticancer drug such as Iressa (generic name: gefitinib) or Tarceva (generic name: erlotinib) causes a serious side effect called diffuse alveolar damage in some cases. Also in acute exacerbation of idiopathic pulmonary fibrosis, the serious side effect called diffuse alveolar damage is caused in some cases. Diffuse alveolar damage shows resistance to treatment, has a recurrent nature, and exhibits repeated exacerbation during treatment, resulting in serious exacerbation at an early stage. Thus, diffuse alveolar damage is a symptom to which very careful attention should be paid.

Japanese are reported to develop such diffuse alveolar damage at high frequency (Non-patent Document 1). For example, in cases of gefitinib, the frequency is 0.3% according to surveys in countries other than Japan, while the frequency is 3.98% in Japanese, which indicates a not less than 10 times higher frequency in Japanese. In cases of erlotinib, the frequency is 0.2% according to surveys on Asians, while the frequency is 2.7% according to a survey on Japanese, which again indicates a not less than 10 times higher frequency in Japanese. Further, Japanese patients with idiopathic pulmonary fibrosis are reported to show a higher rate of acute exacerbation and a higher case fatality rate than patients in other countries (Non-patent Document 2). It has been assumed that the number of deaths due to diffuse alveolar damage in Japan is as much as several thousand per year. It should be noted, of course, that death due to the side effect of drugs is a serious problem also in countries other than Japan, apart from its frequency.

PRIOR ART DOCUMENTS

Non-Patent Documents

Non-patent Document 1: JMAJ (Japan Medical Association), vol. 50, p. 107 (2007);
Non-patent Document 2: Am J Respir Crit Care Med. vol. 177(12), pp. 1397-1398 (2008).

SUMMARY OF THE INVENTION

Technical Problem

Anticancer drug therapy is carried out, of course, for treatment of cancer. However, as described above, there are cases where diffuse alveolar damage occurs due to administration of an anticancer drug. Since diffuse alveolar damage shows rapid progression and a high case fatality rate, it would be very useful if a method for preliminarily determining the risk of development of diffuse alveolar damage due to administration of an anticancer drug can be provided. This is because the method enables prevention of death of a cancer patient due to an anticancer drug, which should originally be administered for the purpose of saving the life of the patient.

In general, diffuse alveolar damages including those caused by administration of anticancer drugs cannot be easily distinguished from normal pneumonia based on their initial symptoms. At clinical sites, these diseases often cannot be distinguished from each other at the first visit, and, in such cases, treatment is carried out from the viewpoints of both pneumonia and diffuse alveolar damage. Since diffuse alveolar damage shows rapid progression and a high case fatality rate, it would be very useful if a method for preliminarily determining the risk of development of diffuse alveolar damage can be provided at the time point when the initial symptoms are found.

However, in spite of the past efforts by research institutes around the world, gene polymorphisms associated with diffuse alveolar damage have not been discovered. Therefore, needless to say, no gene polymorphism has been reported to have very strong association with diffuse alveolar damage so far. Although there may be many reasons for this, one of the reasons may be difficulty in obtaining samples from patients since the patients die at an early stage due to drastic exacerbation of the disease state.

Under such circumstances, the present invention aims to provide: (1) a method for determining the risk of development of diffuse alveolar damage, which method comprises detecting an MUC4 gene polymorphism(s); (2) a method for determining the risk of occurrence of a side effect in an anticancer drug therapy, which method comprises detecting an MUC4 gene polymorphism(s); (3) a kit used for these purposes; and the like.

Technical Solution

In order to solve the problems described above, the present invention has the following characteristics.

That is, an embodiment of the present invention is a method for determining the risk of development of diffuse alveolar damage, which method comprises detecting a gene polymorphism(s) present in the MUC4 gene.

In an embodiment of the present invention, the "gene polymorphism(s) present in the MUC4 gene" may be a gene polymorphism(s) present in exon 2 of the MUC4 gene.

In an embodiment of the present invention, the "gene polymorphism(s) present in exon 2 of the MUC4 gene" may be at least one single nucleotide polymorphism selected from the group consisting of the following (1) to (6):

(1) rs150551454 (C/T polymorphism at nucleotide position 195,507,491 in chromosome 3);

(2) rs62282480 (C/A polymorphism at nucleotide position 195,510,749 in chromosome 3);

(3) rs2911272 (A/G polymorphism at nucleotide position 195,510,773 in chromosome 3);

(4) rs413807 (C/T polymorphism at nucleotide position 195,510,827 in chromosome 3);

(5) rs6805660 (T/C polymorphism at nucleotide position 195,512,042 in chromosome 3); and (6) rs62282486 (T/C polymorphism at nucleotide position 195,512,245 in chromosome 3).

In an embodiment of the present invention, the "gene polymorphism(s) present in exon 2 of the MUC4 gene" may be the following single nucleotide polymorphisms (5) and (6):

(5) rs6805660 (T/C polymorphism at nucleotide position 195,512,042 in chromosome 3); and (6) rs62282486 (T/C polymorphism at nucleotide position 195,512,245 in chromosome 3).

In an embodiment of the present invention, the diffuse alveolar damage is caused by administration of a drug. The drug may be an anticancer drug. Such an anticancer drug may be selected from the group consisting of molecular-targeted agents, antimetabolites, and microtubule depolymerization inhibitors. Specific examples of such an anticancer drug include gefitinib, erlotinib, crizotinib, gemcitabine, irinotecan, pemetrexed, and docetaxel.

In an embodiment of the present invention, the diffuse alveolar damage may be caused by acute exacerbation of idiopathic pulmonary fibrosis.

An embodiment of the present invention relates to a method for determining the risk of occurrence of a side effect in an anticancer drug therapy, which method comprises detecting a gene polymorphism(s) present in the MUC4 gene in a patient to whom an anticancer drug is to be administered. The side effect may be diffuse alveolar damage. Specific examples of such an anticancer drug include gefitinib, erlotinib, crizotinib, gemcitabine, irinotecan, pemetrexed, and docetaxel.

An embodiment of the present invention relates to a kit for determining the risk of development of diffuse alveolar damage, which kit detects a gene polymorphism(s) present in the MUC4 gene.

Effects of the Invention

According to the present invention, a method for determining the risk of occurrence of a side effect in an anticancer drug therapy can be provided. This might enable determination of the risk of occurrence of a side effect before administration of an anticancer drug, and selection of an appropriate therapeutic method for saving the life of a cancer patient. For example, in cases where the risk of occurrence of the side effect, diffuse alveolar damage, due to an anticancer drug is found to be very high, administration of the anticancer drug may be stopped, or the dose of the anticancer drug may be reduced. The method for determining the risk of occurrence of a side effect in an anticancer drug therapy of the present invention may be also useful for patients who are already receiving the anticancer drug.

According to the present invention, a method and a kit for determining the risk of development of diffuse alveolar damage can be provided. By this, the risk of development of alveolar damage can be determined, and an appropriate treatment can be carried out for a patient.

DETAILED DESCRIPTION

Figure 1:
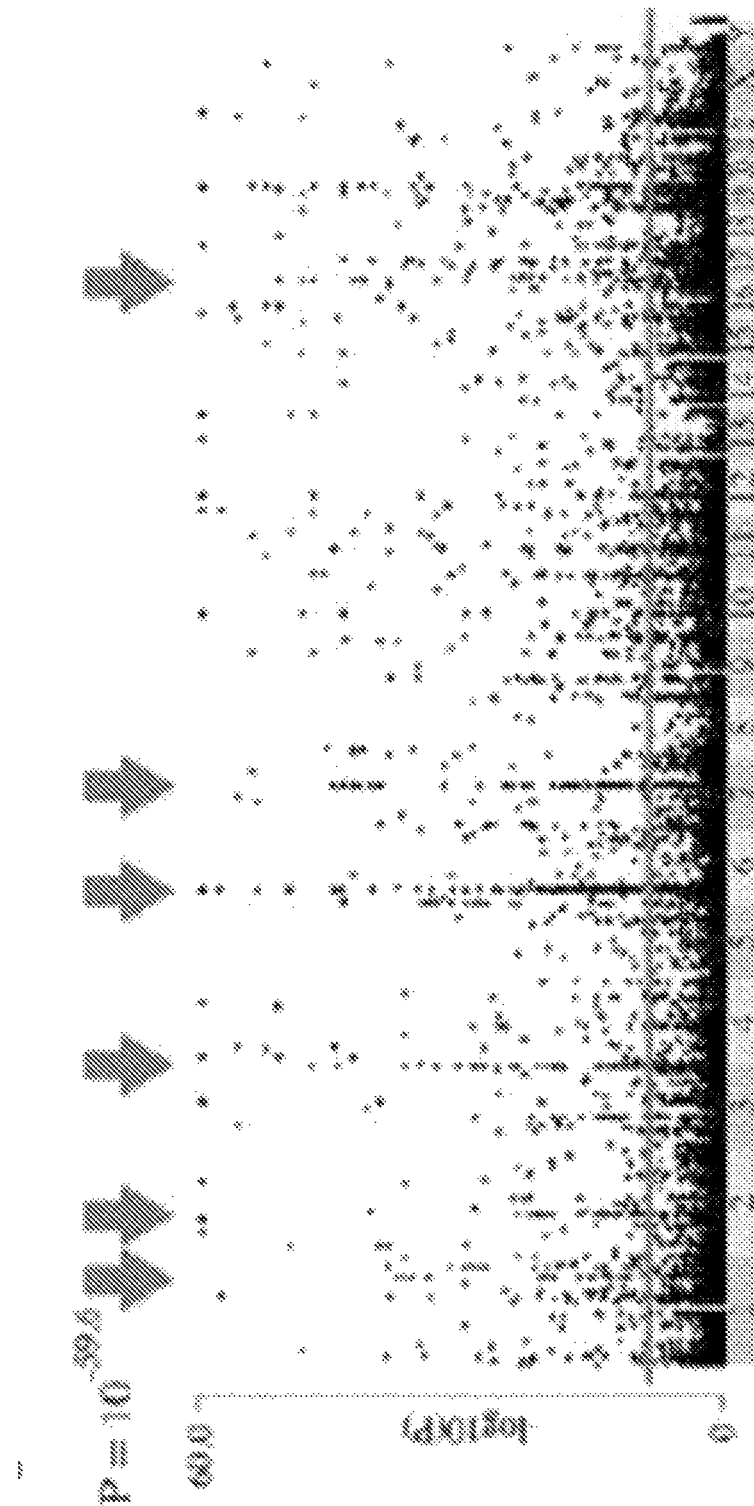
FIG. 1 is a diagram showing an association analysis for mutations in the entire gene coding region between "Iressa ILD+Tarceva ILD" patients and normal Japanese.

The present invention relates to a method and a kit for determining the risk of development of diffuse alveolar damage, and a method for determining the risk of occurrence of a side effect in an anticancer drug therapy, comprising detecting an MUC4 gene polymorphism(s).

<Diffuse Alveolar Damage>

One of the most characteristic symptoms of diffuse alveolar damage (DAD) is inflammation of the entire lung Diffuse alveolar damage may be caused by administration of a drug. Diffuse alveolar damage may also be caused by acute exacerbation of idiopathic pulmonary fibrosis.

Other possible causes of diffuse alveolar damage include the followings:

(1) irradiation pneumonitis that widely extends into areas other than the irradiation field in the lung;

(2) rapid progressive interstitial pneumonia (RPIP), which is found after administration of an anticancer drug to, or after surgery of, a patient with complication of pulmonary fibrosis;

(3) fatal rapidly progressive interstitial pneumonia found in patients with dermatomyositis;

(4) rapid progressive interstitial pneumonia found in patients with interstitial pneumonia other than idiopathic pulmonary fibrosis (IPF); and (5) acute respiratory distress syndrome (ARDS).

<Anticancer Drugs>

As described above, diffuse alveolar damage may be caused by anticancer drugs. Specific examples of such anticancer drugs include, but are not limited to, gefitinib (trade name: Iressa and the like), erlotinib (trade name: Tarceva and the like), crizotinib (trade name: Xalkori and the like), gemcitabine, irinotecan, pemetrexed (trade name: Alimta and the like), and docetaxel (trade name: Taxotere and the like).

Among these, gefitinib, erlotinib, and crizotinib are anticancer drugs categorized as tyrosine kinase inhibitors, which are included in the so called molecular-targeted agents. Gemcitabine, irinotecan, and pemetrexed are anticancer drugs categorized as antimetabolites. Docetaxel is an anticancer drug categorized as a microtubule depolymerization inhibitor.

<Molecular-Targeted Agents>

Molecular-targeted agents are anticancer drugs that suppress the growth and the like of tumors by targeting and inhibiting molecules involved in the growth, infiltration, and metastasis of the tumors. Molecular-targeted agents can be roughly classified into low molecular weight compounds and monoclonal antibodies. Molecular-targeted agents which are low molecular weight compounds can be further classified into tyrosine kinase inhibitors, Raf kinase inhibitors, TNF-α inhibitors, and proteasome inhibitors.

<Tyrosine Kinase Inhibitors>

Examples of known tyrosine kinase inhibitors include gefitinib, erlotinib, and crizotinib as described above, and also include imatinib, dasatinib, vandetanib, sunitinib, lapatinib, and nilotinib. Both gefitinib and erlotinib are known to be anticancer drugs that suppress the growth and the like of tumors by selectively inhibiting the tyrosine kinase of epidermal growth factor receptor to block its signal transduction. Crizotinib is known as an anticancer drug that suppresses the growth and the like of tumors by inhibiting the tyrosine kinase activity of anaplastic lymphoma kinase (ALK), which is a receptor-type tyrosine kinase.

<Antimetabolites>

Antimetabolites are analogues of nucleic acid bases, and are anticancer drugs that suppress the growth and the like of tumors by being incorporated into the DNA strand to stop extension of the DNA strand or to cleave the DNA strand. Gemcitabine is an analogue of a nucleic acid base cytidine. When it is incorporated into a DNA strand, and another nucleic acid base is attached thereto, extension of the DNA strand stops. Irinotecan is a derivative of camptothecin, which is a plant alkaloid, and is an anticancer drug that suppresses the growth and the like of tumors by inhibiting recombination after cleavage of a single-strand DNA by topoisomerase I. Pemetrexed is an antifolate having a molecular structure similar to that of folic acid, and inhibits synthesis of purine and pyrimidine nucleotide precursors by inhibition of thymidylate synthase, dihydrofolate reductase, and glycinamide ribonucleotide formyl transferase.

<Microtubule Depolymerization Inhibitors>

These are anticancer drugs that suppress the growth and the like of tumors by inhibiting depolymerization of microtubules. They bind to microtubules, which are the main constituent of the mitotic apparatus formed during cell division, to prevent the microtubules from undergoing depolymerization and returning to tubulin. This causes stabilization and excessive formation of microtubules, resulting in arrest of the cell cycle in the G2/M phase, and inhibition of cell division. Representative examples of microtubule depolymerization inhibitors include docetaxel and paclitaxel.

<Idiopathic Pulmonary Fibrosis and its Acute Exacerbation>

Idiopathic pulmonary fibrosis (IPF) is a chronic disease, and is an intractable (incurable) disease specified by the Ministry of Health, Labour and Welfare. Patients with this disease suffer from chronic lung destruction, and die of respiratory failure, infection, acute exacerbation, and the like. In ⅓ of IPF patients, the disease state changes from a chronic state to rapidly progressive respiratory failure, leading to death of the patients. This is the acute exacerbation of idiopathic pulmonary fibrosis (IPF AE). The death rate of IPF AE is 70%, which is very high. It is known that patients with IPF die at a high rate due to development of IPF AE after the patients undergo administration of an anticancer drug, radiation therapy, surgery, or the like.

<MUC4 Gene>

The method of the present invention is a method for determining the risk of development of diffuse alveolar damage by detection of at least one gene polymorphism present in the MUC4 gene.

The MUC4 gene is known as a gene encoding the core protein of mucin expressed in the respiratory epithelium. The nucleotide sequence of the MUC4 gene is known and deposited as, for example, NM_018406 according to The National Center for Biotechnology Information (NCBI), and is present at nucleotide positions 195,473,636-195,541,844 (including the nucleotide positions of 3000 base pairs of the promoter region) of chromosome 3 in the human genome UCSC hg19 NCBI b37.3. The nucleotide sequence deposited as NM_018406 is shown in SEQ ID NO:1 as the most typical MUC4 gene coding sequence (cDNA sequence), and the amino acid sequence of the protein encoded by the nucleotide sequence is shown in SEQ ID NO:2.

In the present invention, the method for determining the risk of development of diffuse alveolar damage is a method comprising detecting an MUC4 gene polymorphism(s). The "comprising" herein means that the process of detecting the MUC4 gene polymorphism(s) is the substantial part of the method for determining the risk of development of diffuse alveolar damage, and that the method may also comprise other processes.

The detection of the MUC4 gene polymorphism(s) is preferably detection of one or more single nucleotide polymorphisms present in exon 2 of the MUC4 gene (nucleotide positions 195,518,368-195,505,661 in chromosome 3), especially preferably detection of at least one single nucleotide polymorphism selected from the group consisting of the following (1) to (6) (wherein rs means reference SNP ID):

(1) rs150551454 (C/T polymorphism at nucleotide position 195,507,491 in chromosome 3);

(2) rs62282480 (C/A polymorphism at nucleotide position 195,510,749 in chromosome 3);

(3) rs2911272 (A/G polymorphism at nucleotide position 195,510,773 in chromosome 3);

(4) rs413807 (C/T polymorphism at nucleotide position 195,510,827 in chromosome 3);

(5) rs6805660 (T/C polymorphism at nucleotide position 195,512,042 in chromosome 3); and (6) rs62282486 (T/C polymorphism at nucleotide position 195,512,245 in chromosome 3).

<Method for Detecting Gene Polymorphism(s)>

As the method for detecting at least one single nucleotide polymorphism selected from the group consisting of the above-described (1) to (6) in the MUC4 gene, a known method which is commonly used as a method for detecting a polymorphism(s) in a nucleic acid sequence may be used as appropriate, and examples of such a method include replication or amplification of nucleic acid, and hybridization and sequencing using a probe(s).

For example, direct detection of a polymorphism(s) in the MUC4 gene is possible by amplifying a nucleic acid fragment containing the position(s) where the polymorphism(s) of the MUC4 gene is/are present, and determining the sequence of the amplified nucleic acid product using a sequencer. A preferred method for the replication or amplification of the nucleic acid is PCR. However, the method is not limited thereto, and known methods such as the LAMP method, NASBA method, LCR method, and SDA method may also be used. The polymorphism(s) of the MUC4 gene may also be detected by real-time PCR using a TaqMan probe wherein hybridization of the TaqMan probe to a specific fragment containing the MUC4 gene polymorphism(s) is detected.

In the PCR, a forward primer and a reverse primer are used. These primers can be designed based on the DNA sequence at a position where detection of the polymorphism(s) of the MUC4 gene is possible. For example, the primers may be designed such that one or more of the single nucleotide polymorphisms (1) to (6) identified in the present invention is sandwiched between the forward primer and the reverse primer. Alternatively, at least one of the forward primer and the reverse primer may be designed at the position(s) of a single nucleotide polymorphism(s) such that amplification occurs (or does not occur) only in cases where the genetic polymorphism(s) is/are present.

The length of each primer is not limited as long as a sufficient amount of amplified DNA fragments can be obtained, and depends on the GC content and the like of the sequence selected. The length of the primer sequence is preferably about 10 to 100 bases, more preferably 10 to 50 bases.

In the hybridization using a probe, a portion containing one or more of the single nucleotide polymorphisms (1) to (6) may be used as the probe. The probe may be labeled with a fluorescent substance, radioactive substance, or the like, if necessary. The probe is not limited as long as the probe can detect the single nucleotide polymorphism(s). That is, as long as the presence/absence of the single nucleotide polymorphism(s) can be determined based on the presence/absence of hybridization of the probe or based on the detected intensity, the length of the probe is not limited, and the probe may contain one or more substitution(s), deletion(s), and/or addition(s) compared to the subject sequence to be hybridized therewith. Conditions of the hybridization may be appropriately determined depending on the length and the GC content of the probe, and the like.

The detection of the single nucleotide polymorphism(s) can also be carried out by the restriction fragment length polymorphism (RFLP) method and/or electrophoresis. By performing digestion using a restriction enzyme that recognizes and specifically cleaves a sequence(s) containing the position(s) of the single nucleotide polymorphism(s), and investigating the size(s) of the obtained fragment(s) by electrophoresis, the presence/absence of the cleavage by the restriction enzyme can be detected. This allows detection of the polymorphism(s). Single strand conformation polymorphism (SSCP) analysis and/or capillary electrophoresis may also be used.

<Kit for Determining Risk of Development of Diffuse Alveolar Damage>

In the present invention, the kit for determining the risk of development of diffuse alveolar damage is a kit containing a reagent(s) to be used for the above-described method for detecting a polymorphism(s) of the MUC4 gene. Examples of the reagent(s) include those generally used in the methods for detecting gene polymorphism(s) described above, such as commercially available reagents and synthetic oligonucleotide DNAs. For example, in cases of PCR analysis, the kit may contain a forward primer and a reverse primer for amplification of the DNA fragment of interest, four kinds of deoxyribonucleoside triphosphates, DNA polymerase, and the like.

The terms used in the present description are merely for explanation of specific modes, and not intended to limit the invention.

The term "contain/comprise" used in the present description is intended to mean the presence of a described matter(s) (member(s), step(s), element(s), number(s), and/or the like), and does not exclude the presence of one or more of other matters (members, steps, elements, numbers, and the like) except for cases where the context evidently requires a different understanding.

Unless otherwise defined, all terms used herein (including technical terms and scientific terms) have the same meanings as the meanings widely understood by those skilled in the art to which the present invention belongs. Unless otherwise clearly defined, the terms used herein should be understood to have meanings consistent with the present description and with the meanings in the related technical fields, and should not be understood to have idealized meanings or excessively formal meanings.

Terms such as "first" and "second" are used to represent various elements in some cases. It is understood that these elements should not be limited by those terms. These terms are used merely for distinguishing an element from another element, and, for example, a first element may be described as a second element, or a second element may be similarly described as a first element, without departing from the scope of the present invention.

The present invention is described below more specifically by way of Examples. However, the present invention can be realized in various modes, and should not be understood as being limited by the Examples described here.

EXAMPLES

Example 1

<Patient Samples>

From 30 cooperative medical institutions throughout Japan, a total of 442 cases of patient samples, including 262 cases of patients diagnosed with drug-induced lung damage and 180 cases of patients diagnosed with interstitial lung disease, were collected.

The 180 cases of patients diagnosed with interstitial lung disease include 141 cases of IPF acute exacerbation patients.

The 262 cases of patients diagnosed with drug-induced lung damage include the following cases.

49 cases of patients with interstitial lung disease (ILD) caused by Iressa or Tarceva (hereinafter referred to as "Iressa ILD+Tarceva ILD")

3 cases of patients with interstitial lung disease (ILD) caused by Xalkori (hereinafter referred to as Xalkori ILD)

38 cases of patients with interstitial lung disease (ILD) caused by Taxotere (hereinafter referred to as Taxotere ILD).

<Exome Analysis>

Patient data and patient images were collected for 279 cases out of the 442 cases described above, for confirmation of the diagnosis. Among definitely diagnosed cases, 98 patients (36 "Iressa ILD+Tarceva ILD" patients, 45 IPF acute exacerbation patients, 2 Xalkori ILD patients, and 15 Taxotere ILD patients) selected mainly from fulminant cases and fatal cases (who are thought to be patients who developed diffuse alveolar damage) were subjected to human entire gene coding region sequence analysis (exome analysis).

To provide controls, exome fastq data for Caucasians (53 individuals), Chinese Hans (68 individuals), and Japanese (70 individuals) were obtained from a sequence read archive database (http://www.ncbi.nlm.nih.gov/sra). All data were mapped on a human genome reference sequence (hg19) using CLC Genomics Workbench (CLC bio). After confirming that not less than 90% of the exon regions were read not less than 10 times in each patients, information on gene mutations was obtained using the Probabilistic variant detection algorithm.

As a result, among the mutations detected in any one or more of the Japanese (98 patients+70 controls), mutations that cause amino acid changes (non-synonymous mutations) were present at 180,215 positions in the whole genome.

(Example 2) <"Iressa ILD+Tarceva ILD" Patients>

(Example 2-1) <Association Analysis>

For all 180,215 polymorphisms described above, association analysis was carried out between a total of 36 "Iressa ILD+Tarceva ILD" patients and 70 normal Japanese. The results are shown in FIG. 1. Bonferroni correction was carried out, and associations with P values of not more than 0.001/180,215 were regarded as significant.

In FIG. 1, isolated points could be artifacts due to differences in the exon complement efficiency among kits. The points contained in the areas where the points aggregate in spire shapes (for example, the positions indicated by arrowheads in FIG. 1) indicate that there are differences in the polymorphism frequency between the two groups over a large chromosomal region, and are likely to suggest true associations.

(Example 2-2) <Identification of Gene Polymorphisms>

Only polymorphisms that showed significant P values in <Association Analysis> in Example 2-1 were selected, and subjected to international comparison of the frequency.

For Iressa ILD and Tarceva ILD, the following epidemiological data are known.

(1) The frequency of development in Japanese is about 4%.

(2) The frequency of development in Westerners is not more than 1/10 of the frequency in Japanese.

(3) The frequency of development in Chinese is not more than the frequency of development in Japanese.

From the viewpoint of the epidemiological data described above, each polymorphism was evaluated based on the exome data obtained in Example 1 for the Japanese (70 individuals), Caucasians (53 individuals), and Chinese Hans (68 individuals), in terms of:

the probability that the frequency of Japanese carrying the gene is not less than 4% (P1);

the probability that the frequency of Westerners carrying the gene is not more than 1/10 of the frequency of Japanese carrying the gene (P2); and the probability that the frequency of Chinese carrying the gene is not more than the frequency of Japanese carrying the gene (P3);

and the probability that all of these are satisfied, P(P1×P2×P3), was calculated.

The probability P can be understood as the probability that each polymorphism is consistent with the epidemiological data described above. The results are shown in FIG. 2.

Figure 2:
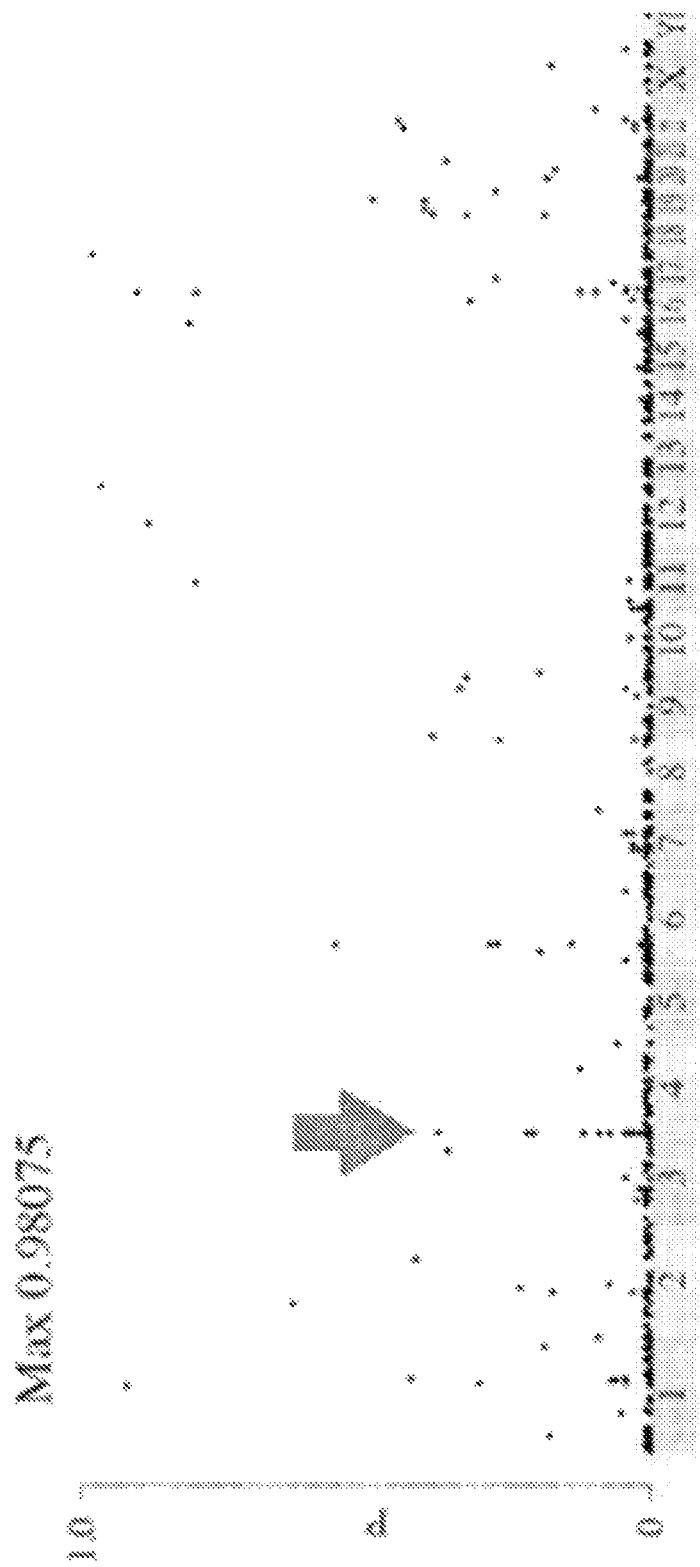
FIG. 2 is a diagram showing the probabilities at which the polymorphisms satisfy epidemiological data.

Each of all points with P>0.1 in FIG. 2 was studied in terms of the gene function to which it belongs and the gene expression site. As a result, MUC4 (which corresponds to the position indicated by the arrowhead in FIG. 2) was the only gene that is expressed in lung and has a function which could be associated with interstitial lung disease.

(Example 2-3) <Identification of Gene Polymorphisms in MUC4>

By the same method as in <Exome Analysis> in Example 1, all mutations in the MUC4 gene region were specified.

All these mutations were subjected to association analysis for a total of 36 "Iressa ILD+Tarceva ILD" patients and 70 normal Japanese. In <Association Analysis> in Example 2-1, only mutations that cause amino acid changes (non-synonymous mutations) were used. However, in the present analysis, all mutations were used irrespective of whether each mutation is a mutation that causes an amino acid change (non-synonymous mutation).

Figure 3:
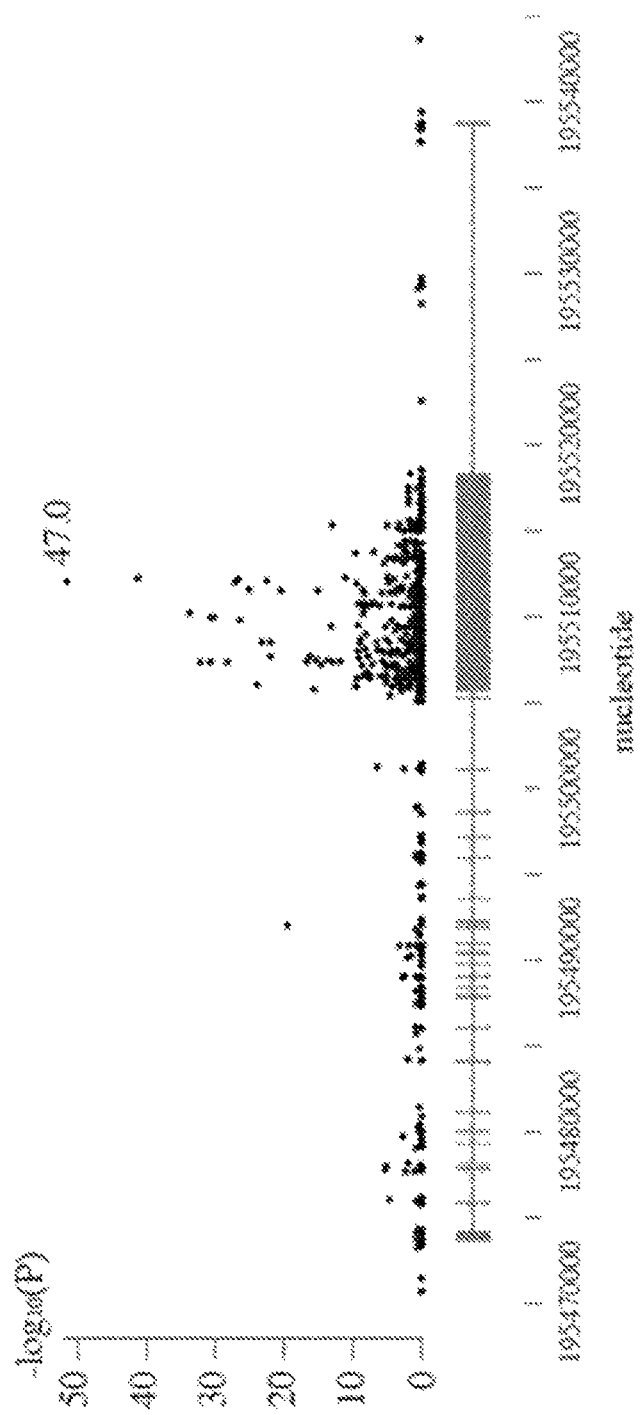
FIG. 3 is a diagram showing an association analysis for mutations in the MUC4 region between "Iressa ILD+Tarceva ILD" patients and normal Japanese.

The results are shown in FIG. 3. Since MUC4 is present in the reverse strand, the right side corresponds to the 5' side in FIG. 3. The part corresponding to exon 2 (nucleotide positions 195,505,661-195,518,368) contained an especially large number of mutations.

In exon 2, the following positions showed especially strong associations: rs150551454 (nucleotide position 195,507,491), rs62282480 (nucleotide position 195,510,749), rs2911272 (nucleotide position 195,510,773), rs413807 (nucleotide position 195,510,827), rs6805660 (nucleotide position 195,512,042), and rs62282486 nucleotide position 195,512,245). Among these, the following positions showed extremely strong associations: rs6805660 (nucleotide position 195,512,042) and rs62282486 (nucleotide position 195,512,245).

(Example 2-4) <Relationship Between Gene Polymorphisms and Diseases>

The frequencies of polymorphisms of rs6805660 and rs62282486, which showed the strongest associations, were studied. The results are shown in Table 1. In Table 1, Ref/Ref represents the homozygote of the human genome reference sequence; Alt/Alt represents the homozygote of the mutant sequence; and Ref/Alt represents the heterozygote.

TABLE 1

|  | Caucasians Ref/ RefRef/ AltAlt/ Alt | | | Chinese Hans Ref/ RefRef/ AltAlt/ Alt | | | Japanese Ref/ RefRef/ AltAlt/ Alt | | | "Iressa ILD + Tarceva ILD" patients Ref/ RefRef/ AltAlt/ Alt | | |
|---|---|---|---|---|---|---|---|---|---|---|---|---|
| rs6805660 | 51 | 0 | 2 | 68 | 0 | 0 | 65 | 0 | 5 | 0 | 0 | 36 |
| rs62282486 | 53 | 0 | 0 | 68 | 0 | 0 | 67 | 0 | 3 | 2 | 0 | 34 |

Surprisingly, as is evident from Table 1, all "Iressa ILD+Tarceva ILD" patients (that is, patients who developed diffuse alveolar damage, as described in Example 1) had the mutant sequence of rs6805660 as a homozygote, and all of these patients except 2 cases had the mutant sequence of rs62282486 as a homozygote. That is, among the patients with diffuse alveolar damage caused by these drugs, 100% (36/36) had the mutant sequence of rs6805660, and about 95% (34/36) had the mutant sequence of rs62282486. It is very surprising that such extremely strong associations were found.

Among the 70 normal Japanese, only 5 individuals had the mutant sequence of rs6805660 as a homozygote, and only 3 individuals had the mutant sequence of rs62282486 as a homozygote. Either of these mutations is present in only about 4% to about 7% of normal Japanese.

It should be noted that exon 2 is the variable number of tandem repeat (VNTR) region of MUC4. Although rs6805660 and rs62282486 cause amino acid mutations, there is also a possibility that these are associated with the number of VNTRs.

(Example 3) <IPF Acute Exacerbation Patients>

Figure 4:
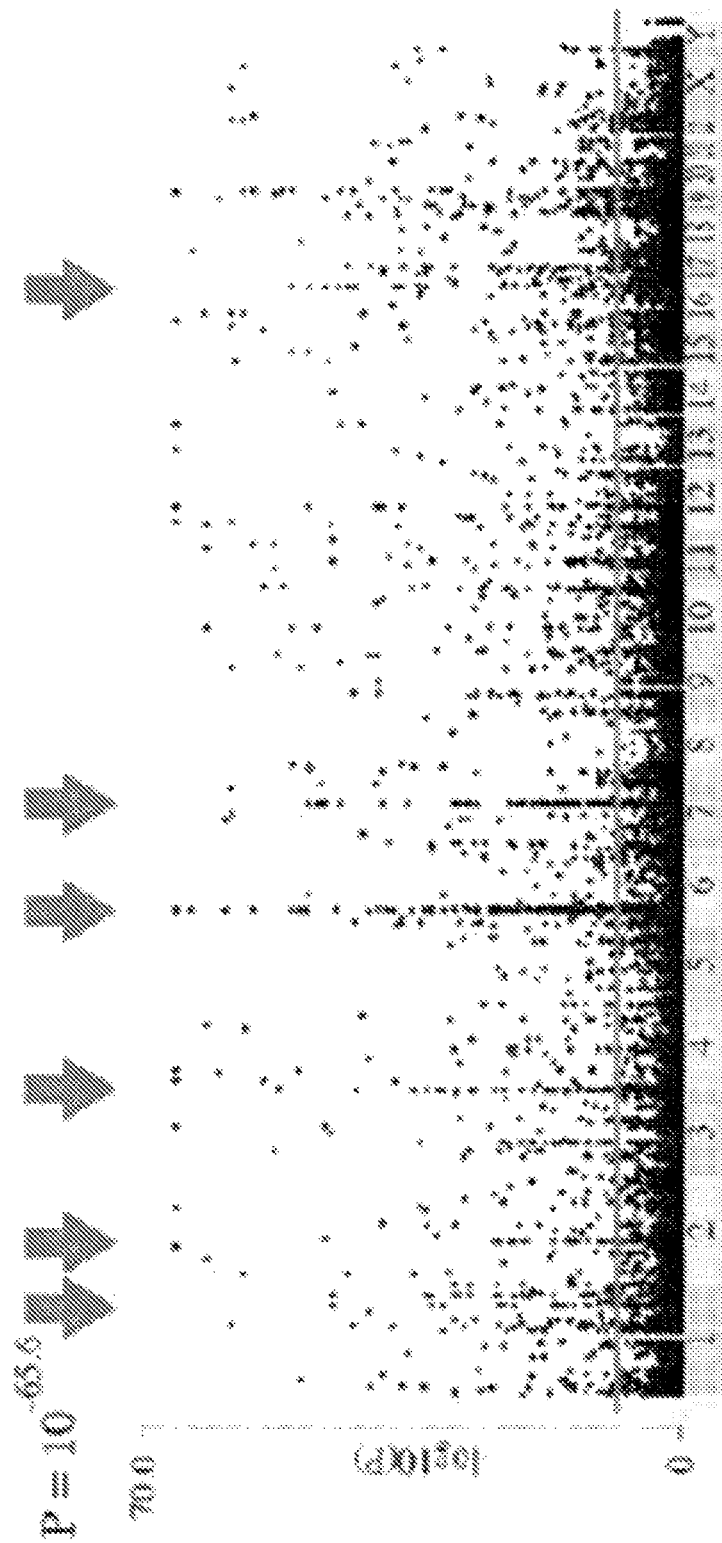
FIG. 4 is a diagram showing an association analysis for mutations in the entire gene coding region between IPF acute exacerbation patients and normal Japanese.

By the same method as in <Association Analysis> in Example 2-1, association analysis was carried out between the 45 IPF acute exacerbation patients and the 70 normal Japanese. The results are shown in FIG. 4.

Figure 5:
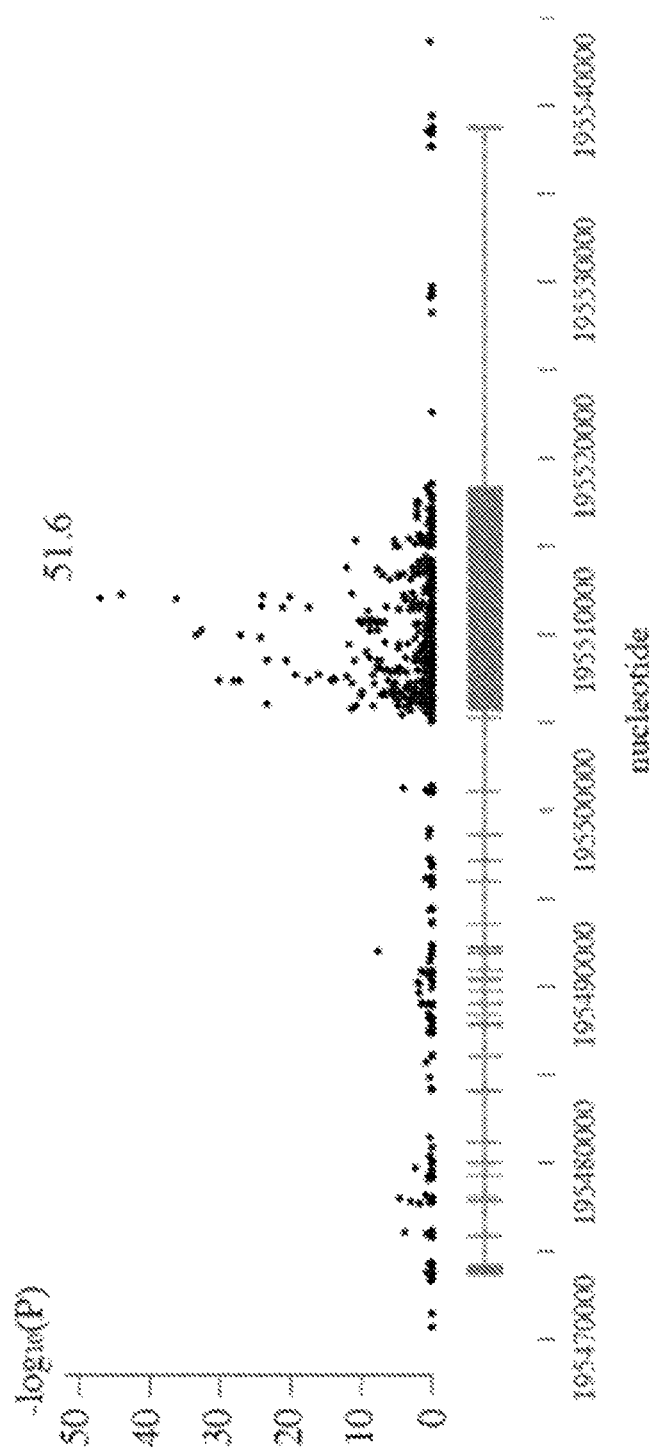
FIG. 5 is a diagram showing an association analysis for mutations in the MUC4 region between IPF acute exacerbation patients and normal Japanese.

In addition, by the same method as in <Identification of Gene Polymorphisms in MUC4> in Example 2-3, association analysis was carried out between the 45 IPF acute exacerbation patients and the 70 normal Japanese. The results are shown in FIG. 5. Since MUC4 is present in the reverse strand, the right side corresponds to the 5' side in FIG. 5. The part corresponding to exon 2 (nucleotide positions 195,505,661-195,518,368) contained an especially large number of mutations.

In exon 2, the following positions showed extremely strong associations: rs6805660 (nucleotide position 195,512,042) and rs62282486 (nucleotide position 195,512,245).

In addition, by the same method as in <Relationship between Gene Polymorphisms and Diseases> in Example 2-4, the frequencies of polymorphisms of rs6805660 and rs62282486, which showed the strongest associations, were studied. The results are shown in Table 2. In Table 2, Ref/Ref represents the homozygote of the human genome reference sequence; Alt/Alt represents the homozygote of the mutant sequence; and Ref/Alt represents the heterozygote.

TABLE 2

|  | Caucasians Ref/ RefRef/ AltAlt/ Alt | | | Chinese Hans Ref/ RefRef/ AltAlt/ Alt | | | Chinese Hans Ref/ RefRef/ AltAlt/ Alt | | | IPF acute exacerbation patients Ref/ RefRef/ AltAlt/ Alt | | |
|---|---|---|---|---|---|---|---|---|---|---|---|---|
| rs6805660 | 51 | 0 | 2 | 68 | 0 | 0 | 65 | 0 | 5 | 0 | 0 | 45 |
| rs62282486 | 53 | 0 | 0 | 68 | 0 | 0 | 67 | 0 | 3 | 5 | 0 | 40 |

Surprisingly, as is evident from Table 2, all "IPF acute exacerbation" patients (that is, patients who developed diffuse alveolar damage, as described in Example 1) had the mutant sequence of rs6805660 as a homozygote, and all of these patients except 5 cases had the mutant sequence of rs62282486 as a homozygote. That is, among the patients with diffuse alveolar damage caused by these drugs, 100% (45/45) had the mutant sequence of rs6805660, and about 89% (40/45) had the mutant sequence of rs62282486. It is very surprising that such extremely strong associations were found.

As described above, among the 70 normal Japanese, only 5 individuals had the mutant sequence of rs6805660 as a homozygote, and only 3 individuals had the mutant sequence of rs62282486 as a homozygote. Either of these mutations is present in only about 4% to about 7% of normal Japanese.

(Example 4) <Taxotere ILD Patients and Xalkori ILD Patients>

By the same method as in <Relationship between Gene Polymorphisms and Diseases> in Example 2-4, the frequencies of polymorphisms of rs6805660 and rs62282486 were studied also for the 15 Taxotere ILD patients and the 2 Xalkori ILD patients. The results are shown in Table 3.

TABLE 3

|  | Japanese Ref/RefRef/ AltAlt/Alt | | | Taxotere ILD patients Ref/RefRef/ AltAlt/Alt | | | Xalkori ILD patients Ref/RefRef/ AltAlt/Alt | | |
|---|---|---|---|---|---|---|---|---|---|
| rs6805660 | 65 | 0 | 5 | 0 | 0 | 15 | 0 | 0 | 2 |
| rs62282486 | 67 | 0 | 3 | 1 | 0 | 14 | 0 | 0 | 2 |

Surprisingly, as is evident from Table 3, all Taxotere ILD patients (that is, patients who developed diffuse alveolar damage, as described in Example 1) had the mutant sequence of rs6805660 as a homozygote, and all of these patients except 1 case had the mutant sequence of rs62282486 as a homozygote. That is, among the patients with diffuse alveolar damage caused by the drug, 100% (15/15) had the mutant sequence of rs6805660, and about 93% (14/15) had the mutant sequence of rs62282486. It is very surprising that such extremely strong associations were found.

Further, surprisingly, as is evident from Table 3, all Xalkori ILD patients (that is, patients who developed diffuse alveolar damage, as described in Example 1) had the mutant sequences of rs6805660 and rs62282486 as homozygotes. It is very surprising that such extremely strong associations were found.

CONCLUSION

As described above, as a result of intensive study, the present inventors discovered that "Iressa ILD+Tarceva ILD" patients, Taxotere ILD patients, Xalkori ILD patients, and IPF acute exacerbation patients who are suffering from diffuse alveolar damage carry specific gene polymorphisms in the MUC4 gene with extremely high probability unlike other populations.

In spite of the past efforts by research institutes around the world, gene polymorphisms associated with diffuse alveolar damage have not been discovered. Therefore, needless to say, no gene polymorphism has been reported to have very strong association with diffuse alveolar damage so far.

The fact that totally the same results could be obtained not only for anticancer drugs belonging to tyrosine kinase inhibitors such as Iressa, Tarceva, and Xalkori, but also for anticancer drugs belonging to microtubule depolymerization inhibitors such as Taxotere, indicates that diffuse alveolar damage has very strong associations with specific gene polymorphisms independent of the action mechanisms of the drugs. Thus, the method of the present invention can be very useful means for determining the risk of development of diffuse alveolar damage due to any anticancer drug or generic drug. This is because the method enables prevention of death of a cancer patient due to an anticancer drug, which should originally be administered for the purpose of saving the life of the patient.

What is claimed is:

1. A method for treating diffuse alveolar damage caused by a drug, the method comprising:
    administering a lower dosage of the drug to a patient in whom a gene polymorphism in MUC4 gene has been detected than a dosage of the drug that would be administered to the same patient if the polymorphism had not been detected;
    wherein the gene polymorphism is a gene polymorphism in exon 2 of MUC4 gene selected from the group consisting of:
    (1) rs150551454 (C/T polymorphism at nucleotide position 195,507,491 in chromosome 3 of NCBI b37.3);
    (2) rs62282480 (C/A polymorphism at nucleotide position 195,510,749 in chromosome 3 of NCBI b37.3);
    (3) rs2911272 (A/G polymorphism at nucleotide position 195,510,773 in chromosome 3 of NCBI b37.3);
    (4) rs413807 (C/T polymorphism at nucleotide position 195,510,827 in chromosome 3 of NCBI b37.3);
    (5) rs6805660 (T/C polymorphism at nucleotide position 195,512,042 in chromosome 3 of NCBI b37.3); and
    (6) rs62282486 (T/C polymorphism at nucleotide position 195,512,245 in chromosome 3 of NCBI b37.3).

2. The method according to claim 1, wherein the gene polymorphism is rs6805660 or rs62282486.

3. The method according to claim 1, wherein the lower dose is 0 mg/kg.

4. The method according to claim 1, wherein the drug is an anticancer drug.

5. The method according to claim 4, wherein the anticancer drug is selected from the group consisting of molecular-targeted agents, antimetabolites, and microtubule depolymerization inhibitors.

6. The method according to claim 4, wherein the anticancer drugs is selected from the group consisting of gefitinib, erlotinib, crizotinib, gemcitabine, irinotecan, pemetrexed, and docetaxel.

7. The method according to claim 1, wherein the diffuse alveolar damage is caused by acute exacerbation of idiopathic pulmonary fibrosis.

8. The method of claim 1, wherein at least one single nucleotide polymorphism selected from the group consisting of the gene polymorphisms (1), (2), (3), (4), (5), and (6) is detected by using at least one agent selected from the group consisting of:
    a) a set of forward primer and reverse primer designed to amplify a sequence that includes at least one of the single nucleotide polymorphisms (1), (2), (3), (4), (5), and (6);
    b) a set of forward primer and reverse primer at least one of which is designed to anneal to a position that includes at least one of the single nucleotide polymorphisms (1), (2), (3), (4), (5), and (6), such that amplification occurs only in cases where the polymorphism is present; and
    c) a labeled probe that hybridizes to at least one of the single nucleotide polymorphisms (1), (2), (3), (4), (5), and (6).

* * * * *

SEQUENCE LISTING

```
<160> NUMBER OF SEQ ID NOS: 2

<210> SEQ ID NO 1
<211> LENGTH: 16819
<212> TYPE: DNA
<213> ORGANISM: Homo sapiens

<400> SEQUENCE: 1
ctcttttgtc ctcttcccag gttccctggc cccttcggag aaacgcactt ggttcgggcc        60
agccgcctga ggggacgggc tcacgtctgc tcctcacact gcagctgctg ggccgtggag       120 cttcccagg gagccagggg gacttttgcc gcagccatga aggggcacg ctggaggagg         180 gtccctggg tgtccctgag ctgcctgtgt ctctgcctcc ttccgcatgt ggtcccagga        240
accacagagg acacattaat aactggaagt aaaactgctg ccccagtcac ctcaacaggc       300
tcaacaacag cgacactaga gggacaatca actgcagctt cttcaaggac ctctaatcag       360
gacatatcag cttcatctca gaaccaccag actaagagca cggagaccac cagcaaagct       420
caaaccgaca ccctcacgca gatgatgaca tcaactcttt tttcttcccc aagtgtacac       480
aatgtgatgg agacagctcc tccagatgaa atgaccacat catttccctc cagtgtcacc       540
aacacactca tgatgacatc aaagactata acaatgacaa cctccacaga ctccactctt       600
ggaaacacag aagagacatc aacagcagga actgaaagtt ctaccccagt gacctcagca       660
gtctcaataa cagctggaca ggaaggacaa tcacgaacaa cttcctggag gacctctatc       720
caagacacat cagcttcttc tcagaaccac tggactcgga gcacgcagac caccagggaa       780
tctcaaacca gcaccctaac acacagaacc acttcaactc cttctttctc tccaagtgta       840
cacaatgtga cagggactgt ttctcagaag acatctcctt caggtgaaac agctacctca       900
tccctctgta gtgtcacaaa cacatccatg atgacatcag agaagataac agtgacaacc       960
tccacaggct ccactcttgg aaacccaggg gagacatcat cagtacctgt tactggaagt      1020
cttatgccag tcacctcagc agccttagta acatttgatc cagaaggaca atcaccagca      1080
actttctcaa ggacttctac tcaggacaca acagcttttt ctaagaacca ccagactcag      1140
agcgtggaga ccaccagagt atctcaaatc aacaccctca cacactcac accggttaca       1200 acatcaactg ttttatcctc accaagtgga ttcaacccaa gtggaacagt ttctcaggag      1260
acattccctt ctggtgaaac aaccacctca tccccttcca gtgtcagcaa tacattcctg      1320
gtaacatcaa aggtgttcag aatgccaacc tccagagact ctactcttgg aaacacagag      1380
gagacatcac tatctgtaag tggaaccatt tctgcaatca cttccaaagt ttcaaccata      1440
tggtggtcag acactctgtc aacagcactc tcccccagtt ctctacctcc aaaaatatcc      1500
acagctttcc acacccagca gagtgaaggt gcagagacca caggacggcc tcatgagagg      1560
agctcattct ctccaggtgt gtctcaagaa atatttactc tacatgaaac aacaacatgg      1620
ccttcctcat tctccagcaa aggccacaca acttggtcac aaacagaact gccctcaaca      1680
tcaacaggtg ctgccactag gcttgtcaca ggaaatccat ctacagggac agctggcact      1740
attccaaggg tccctctaa ggtctcagca atagggggaac caggagagcc caccacatac       1800
tcctcccaca gcaaaactct cccaaaaaca acaggggcag gcgcccagac acaatggaca      1860
caagaaacgg ggaccactgg agaggctctt ctcagcagcc caagctacag tgtgactcag      1920
```

```
atgataaaaa cggccacatc cccatcttct tcacctatgc tggatagaca cacatcccaa    1980
caaattacaa cggcaccatc aacaaatcat tcaacaatac attccacaag cacctctcct    2040
caggaatcac cagctgtttc ccaaaggggt cacactcaag ccccgcagac cacacaagaa    2100
tcacaaacca cgaggtccgt ctcccccatg actgacacca agacagtcac caccccaggt    2160
tcttccttca cagccagtgg gcactcgccc tcagaaattg ttcctcagga cgcacccacc    2220
ataagtgcag caacaacctt tgccccagct cccaccgggg atggtcacac aacccaggcc    2280
ccgaccacag cactgcaggc agcacccagc agccatgatg ccaccctggg gccctcagga    2340
ggcacgtcac tttccaaaac aggtgccctt actctggcca actctgtagt gtcaacacca    2400
gggggcccag aaggacaatg gacatcagcc tctgccagca cctcacctga cacagcagca    2460
gccatgaccc ataccacca ggctgagagc acagaggcct ctggacaaac acagaccagc    2520
gaaccggcct cctcagggtc acgaaccacc tcagcgggca cagctacccc ttcctcatcc    2580
ggggcgagtg gcacaacacc ttcaggaagc gaaggaatat ccacctcagg agagacgaca    2640
aggttttcat caaacccctc cagggacagt cacacaaccc agtcaacaac cgaattgctg    2700
tccgcctcag ccagtcatgg tgccatccca gtaagcacag gaatggcgtc ttcgatcgtc    2760
cccggcacct ttcatcccac cctctctgag gcctccactg cagggagacc gacaggacag    2820
tcaagcccaa cttctcccag tgcctctcct caggagacag ccgccatttc ccggatggcc    2880
cagactcaga ggacaagaac cagcagaggg tctgacacta tcagcctggc gtcccaggca    2940
accgacacct tctcaacagt cccacccaca cctccatcga tcacatccac tgggcttaca    3000
tctccacaaa ccgagaccca cactctgtca ccttcagggt ctggtaaaac cttcaccacg    3060
gccctcatca gcaacgccac ccctcttcct gtcacctacg cttcctcggc atccacaggt    3120
cacaccaccc ctcttcatgt caccgatgct tcctcagtat ccacaggtca cgccaccct    3180
cttcctgtca ccagcccttc ctcagtatcc acaggtcaca ccacccctct tcctgtcacc    3240
gacacttcct cagaatccac aggtcacgtc acccctcttc ctgtcaccag cttttcctca    3300
gcatccacag gtgacagcac ccctcttcct gtcactgaca cttcctcagc atccacaggt    3360
cacgtcaccc ctcttcctgt caccagcctt tcctcagcat ccacaggtga caccaccct    3420
cttcctgtca ctgacacttc ctcagcatcc acaggtcacg ccacctctct tcctgtcacc    3480
gacacttcct cagtatccac aggtcacacc accctcttc ctgtcaccga cacttcctca    3540
gcatccacag gtcacgccac ctctcttcct gtcaccgaca cttcctcagt atccacaggt    3600
cacaccaccc ctcttcatgt cactgatgct tcctcagcat ccacaggtca ggccaccct    3660
cttcctgtca ccagcctttc ctcagtatcc acaggtgaca ccacgcctct tcctgtcact    3720
agcccttcct cagcatccac aggtcacgcc accctcttc ttgtcaccga cacttcctca    3780
gcatccacag gacacgccac ccctcttcct gtcaccgacg cttcctcagt gtccacagat    3840
cacgccacct ctcttcctgt aaccatccct tccgcagcat ccacaggtca caccaccct    3900
cttcctgtca ccgacacttc ctcagcatcc acaggtcagg ccacctctct tcttgtcacc    3960
gacacttcct cagtatccac aggtgacacc acgcctcttc ctgtcactag cacttcctca    4020
gcatccacag gtcacgtcac tcctcttcat gtcaccagcc cttcctcagc atccacaggt    4080
cacgccaccc ctcttcctgt caccagcctt tcctcagcat ccacaggtga ccatgcct    4140
cttcctgtca ctagcccttc ctcagcatcc acaggtgaca ccaccctct tcctgtcacc    4200
gacgcttcct cagtatccac aggtcacacc accctcttc atgtcactga tgcttcctca    4260
gcatccacag gtcaggccac ccctcttcct gtcaccagcc tttcctcagt atccacaggt    4320
```

```
gacaccacgc ctcttcctgt cactagccct tcctcagcat ccacaggtca cgccacccct    4380
cttcttgtca ccgacacttc ctcagcatcc acaggacacg ccaccectct tcctgtcacc    4440 gacgcttcct cagtgtccac agatcacgcc acctctcttc ctgtaaccat cccttccgca    4500
gcatccacag gtcacaccac ccctcttcct gtcaccgaca cttcctcagc atccacaggt    4560
caggccacct ctcttcttgt caccgacact tcctcagtat ccacaggtga caccacgcct    4620
cttcctgtca ctagcacttc ctcagcatcc acaggtcacg tcactcctct tcatgtcacc    4680
agcccttcct cagcatccac aggtcacgcc accctcttc  ctgtcaccag cctttcctca    4740
gcatccacag gtgacaccat gcctcttcct gtcactagcc cttcctcagc atccacaggt    4800
gacaccaccc ctcttcctgt caccgacgct tcctcagtat ccacaggtca caccacccct    4860
cttcctgtca ccagcccttc ctcagcatct acaggtcaca ccaccctct tcctgtcacc    4920 gacacttcct cagcatccaa aggtgacacc accctcttc  ctgtcaccag cccttcctca    4980
gcatctacag gtcacaccac ccctcttcct gtcaccgaca cttcctcagc atccacaggt    5040
gacaccaccc ctcttcctgt caccaatgct tcctcattat ccacaggtca cgccacccct    5100
cttcatgtca ccagcccttc ctcagcatcc acaggtcacg ccaccctct tcctgtcacc    5160 agcacttcct cagcatccac cggtcacgcc accctcttc  ctgtcaccgg cctttcctca    5220
gctaccacag atgacaccac ccgtcttcct gtcaccgacg tttcctcggc atccacaggt    5280
caggccaccc ctcttcctgt caccagcctt tcctcagtat ccacaggtga caccacgcct    5340
cttcctgtca ctagcccttc ctcagcatcc acaggtcacg ccagccctct tcttgtcact    5400
gacgcttcct cagcatccac aggtcaggcc accctcttc  ctgtcaccga cacttcctca    5460
gtatccacag ctcacgccac cccacttcct gtcaccggcc tttcttcagc ttcacagat    5520 gacaccaccc gtcttcctgt caccgacgtt tcctcggcat ccacaggtca ggccatccct    5580
cttcctgtca ccagcccttc ctcagcatcc acaggtgaca ccaccctct tcctgtcacc    5640 gacgcttcct cagcatccac aggtgacacc acctctcttc ctgtcaccat cccttcctca    5700
gcatcttcag gtcacaccac ctctcttcct gtcaccgacg cttcctcagt gtccacaggt    5760
cacgccacct ctcttcttgt caccgacgct tcctcagtat ccacaggtga caccacccct    5820
cttcctgtca ccgacactaa ctcagcatcc acaggtgaca ccaccctct tcatgtcacc    5880 gacgcttcct cagtatccac aggtcacgcc acctctcttc ctgtcaccag cctttcctca    5940
gcatccacag gtgacaccac gcctcttcct gtcactagcc cttcctcagc atcctcaggt    6000
cacaccaccc ctcttcctgt caccgacgct tcctcagtac ccacaggtca cgccacctct    6060
cttcctgtca ccgacgcttc ctcagtgtcc acaggtcacg ccaccctct tcctgtcacc    6120 gacgcttcct cagtgtccac aggtcatgcc accctcttc  cggtcaccga cacttcctca    6180
gtatctacag gacaggccac ccctcttcct gtcaccagcc tttcctcagc atccactggt    6240
gacaccacgc cgcttcctgt caccgatact tcctcagcat ccacaggtca ggacaccct    6300 cttcctgtca ccagcctttc ctcagtatcc acaggtgaca ccacgcctct tcctgtcact    6360
aacccttcct cagcatccac aggtcacgcc accctcttc  ttgtcaccga cgcttcctca    6420
atatccacag gtcacgccac ctctcttctt gtcaccgacg cttcctcagt atccacaggt    6480
cacgccaccg ctcttcatga caccgatgct tcctcattat ccacaggga  caccaccct    6540 cttcctgtca ccagcccttc ctcaacatcc acaggtgaca ccaccctct tcctgtcacc    6600 gaaacttcct cagtatccac aggtcacgcc acctctcttc ctgtcaccga cacttcctca    6660
gcatccacag gtcacgccac ctctcttcct gtcaccgaca cttcctcagc atccacaggt    6720
```

```
cacgccaccc ctcttcctgt caccgacact tcctcagcat ccacaggtca ggccacccct    6780
cttcctgtca ccagcccttc ctcagcatcc acaggtcacg ccatccctct tcttgtcacc    6840
gacacttcct cagcatccac aggacaggcc acccctcttc ctgtcaccag cctttcctca    6900
gcatccacag gtgacaccac ccctcttcct gtcaccgacg cttcctcagt gtccacaggt    6960
cacgccacct ctcttcctgt caccagcctt tcctcagtat ccacaggtga caccactcct    7020
cttcctgtca ctagcccttc ctcagcatcc acaggtcacg ccacccctct tcatgtcacc    7080
gacgcttcct cagcatccac aggtcacgcc acccctcttc ctgtcaccag cctttcctca    7140
gcatccacag gtgacaccac gcctcttcct gtcactagcc cttcctcagc atccacaggt    7200
cacgccaccc ctcttcatgt caccgacgct tcctcagtat ccacaggtga caccacccct    7260
cttcctgtca ccagctcttc ctcagcatcc tcaggtcaca ccacccctct tcctgtcacc    7320
gacgcttcct cagcatccac aggtgacacc accccctcttc ctgtcaccga cacttcctca    7380
gcatccacag gtcacgccac ccatcttcct gtcaccggcc tttcctcagc ttccacaggt    7440
gacaccaccc gtcttcctgt caccaacgtt tcctcggcat ccacaggtca tgccacccct    7500
cttcctgtca ccagcacttc ctcagcatcc acaggtgaca ccacccctct tcctggcacc    7560
gacacttcct cagtatccac aggtcacacc accccctcttc ttgtcaccga cgcttcgtca    7620
gtatccacag gtgacaccac ccgtcttcct gtcaccagcc cttcctcagc atctacaggt    7680
cacaccaccc ctctacctgt caccgacact ccctcagcat ccacaggtga caccacccct    7740
cttcctgtca ccaatgcttc ctcattatcc acacgtcacg ccacctctct tcatgtcacc    7800
agcccttcct cagcatccac aggtcacgcc acctctcttc ctgtcaccga cacttccgca    7860
gcatccacag gtcacgccac ccctcttcct gtcaccagca cttcctcagc atccacaggt    7920
gacaccaccc ctcttcctgt caccgacact tactcagcat ccacaggtca ggccacccct    7980
cttcctgtca ccagccttc ctcagtatcc acaggtgaca ccacgcctct tcctgtcact    8040
agcccttcct cagcatccac aggtcacgcc actcctcttc ttgtcaccga cgcttcctca    8100
gcatccacag gtcaggccac ccctcttcct gtcaccagcc tttcctcagt atccacaggt    8160
gacaccacgc ctcttcctgt cactagcct tcctcagcat ccaccggtca tgccacctct    8220
cttcctgtca ccgacacttc ctcagcatcc acaggtgaca ccacctctct tcctgtcacc    8280
gacacttcct cagcatacac aggtgacacc acctctcttc ctgtcaccga cacttcctca    8340
tcatccacag gtgacaccac ccctcttctt gtcaccgaga cttcctcagt atccacaggt    8400
gacaccaccc ctcttcctgt caccgacact tcctcagcat ccacaggtca cgccacccct    8460
cttcctgtca ccaacacttc ctcagtatcc acaggtcacg ccacccctct tcatgtcacc    8520
agcccttcct cagcatccac aggtcacacc accccctcttc ctgtcaccga cgcttcgtca    8580
gtgtccacag gtcacgccac ctctcttcct gtcaccgacg cttcctcagt gttcacaggt    8640
catgccacct ctcttcctgt caccatccct tcctcagcat cctcaggtca caccacccct    8700
cttcctgtca ccgacgcttc ctcagtgtcc acaggtcacg ccacctctct tcctgtcacc    8760
gacgcttcct cagtgtccac aggtcatgcc accccctcttc ctgtcaccga cgcttcctca    8820
gtgtccacag gtcacgctac ccctcttcct ctcaccagcc tttcctcagt atccacaggt    8880
gacaccacgc ctcttcctgt caccgacact tcctcagcat ccacaggtca ggccacccct    8940
cttcctgtca ccagccttc ctcagtatcc acaggtgaca ccacccctct tcctgtcacc    9000
gacacttcct cagcatccac aggtcacgcc acctctcttc ctgtcaccga cacttcctca    9060
gcatccacag gtcacgccac ccctcttcct gacaccgaca cttcctcagc atccacaggt    9120
```

```
cacgccaccc ttcttcctgt caccgacact tcctcagcat ccataggtca cgccacctct    9180
cttcctgtca ccgacacttc ctcaatatcc acaggtcacg ccacccctct tcatgtcacc    9240
agcccttcct cagcatccac cggtcacgcc acccgcttc ctgtcaccga cacttcctca     9300
gcatccacag gtcacgccaa ccctcttcat gtcaccagcc cttcctcagc atccaccggt    9360
cacgccaccc cgcttcctgt caccgacact tcctcagcat ccacaggtca cgccacccct    9420
cttcctgtca ccagccttc ctcagtatcc acaggtgaca ccacgcctct tcctgtcact    9480
agcccttcct cagcatccac aggtcacacc accctcttc ctgtcaccga cacttcctca    9540
gcatccacag gtcaggccac cgtcttcct gtcaccagca cttcctcagc atccacaggt    9600
gacaccaccc ctcttcctgt caccgacact tcctcagcat ccacaggtca ggccacccct    9660
cttcctgtca ccagccttc ctcagtatcc acaggtgaca ccacgcctct tcctgtcact    9720
agcccttcct cagcatccac aggtcacgcc actcctcttc ttgtcaccga cgcttcctca    9780
gcatccacag gtcaggccac ccctcttcct gtcaccagcc tttcctcagt atccacaggt    9840
gacaccacgc ctcttcctgt cactagccct tcctcagcat ccaccggtca tgccacctct    9900
cttcctgtca ccgacacttc ctcagcatcc acaggtgaca ccacctctct tcctgtcacc    9960
gacacttcct cagcatacac aggtgacacc acctctcttc ctgtcaccga cacttcctca   10020
tcatccacag gtgacaccac ccctcttctt gtcaccgaga cttcctcagt atccacaggt   10080
cacgccactc ctcttcttgt caccgacgct tcctcagcat ccacaggtca cgccacccct   10140
cttcatgtca ccagcccttc ctcagcatcc acaggtgaca ccaccctgt gcctgtcacc    10200 gacacttcct cagtatccac aggtcacgcc accctcttc ctgtcaccgg cctttcctca    10260
gcttccacag gtgacaccac ccgtcttcct gtcaccgaca tttcctcggc atccacaggt   10320
caggccaccc ctcttcctgt caccaacact tcctcagtat ccacaggtga caccatgcct   10380
cttcctgtca ctagcccttc ctcagcatcc acaggtcacg ccacccctct tcctgtcacc    10440
agcacttcct cagcatccac cggtcacgcc accctgttc ctgtcaccag cacttcctca    10500
gcatctacag gtcacaccac ccctcttcct gtcaccgaca cttcctcagc atccacaggt    10560
gacaccaccc ctcttcctgt caccagccct tcctcagcat ctacaggtca caccaccct    10620 cttcatgtca ccatcccttc ctcagcatcc acaggtgaca ccagcactct tcctgtcacc    10680
ggcgcttcct cagcatccac cggtcacgcc accctcttc ctgtcaccga cacttcctca    10740
gtatccaccg gtcacgccac gcctcttcct gtcaccagcc tttcctcagt atccacaggt    10800
gacaccaccc ctcttcctgt caccgacgct tcctcggcat ccacaggtca ggccacccct    10860
cttcctgtca ccagccttc ctcagtatcc acaggtgaca ccacccctct tcttgtcacc    10920
gacgcttcct cagtatccac aggtcacgcc accctcttc ctgtcaccga cacttcctca    10980
gcatccacag gtgacaccac ccgtcttcct gtcacggaca cttcctcagc atccacaggt    11040
caggccaccc ctcttcctgt caccagcctt tcctcagtat ccacaggtga caccaccct    11100 cttcttgtca ccgacgcttc ctcagtatcc acaggtcacg ccacccctct tcctgtcacc    11160
gacacttcct cagcatccac aggtgacacc accgtcttc ctgtcacgga cacttcctca    11220
gcatccacag gtcaggccac ccctcttcct gtcaccatcc cttcctcatc atcctcaggt    11280
cacaccaccc ctcttcctgt caccagcact tcctcagtat ctacaggtca cgtcaccct    11340 cttcatgtca ccagcccttc ctcagcatcc acaggtcacg tcaccctct tcctgtcacc     11400 agcacttcct cagcatccac aggtcacgcc accctcttc ttgtcaccga cgcttcctca    11460
gtgtccacag gtcacgccac gcctcttcct gtcaccgacg cttcctcagc atccacaggt    11520
```

```
gacaccaccc ctcttcctgt caccgacact tcctcagcat ccacaggtca ggccacccct    11580
cttcctgtca ccagccttc ctcagtatcc acaggtgaca ccaccctct tcctgtcacc     11640 gacgcttcct cagcatccac aggtcacgcc acccctcttc ctgtcaccat cccttcctca    11700
gtatccacag gtgacaccat gcctcttcct gtcactagcc cttcctcagc atccacaggt    11760
cacgccaccc ctcttcctgt taccggcctt tcctcagctt ccacaggtga caccacccct    11820
cttcctgtca ccgacacttc ctcagcatcc acacgtcacg ccaccctct tcctgtcacc     11880 gacacttcct cagcttccac agatgacacc acccgtcttc ctgtcaccga cgtttcctcg    11940
gcatccacag gacatgccac ccctcttcct gtcaccagca cttcctcagc atccacaggt    12000
gacaccaccc ctcttcctgt caccgacact tcctcagtat ccaggtca cgccacctct      12060 cttcctgtca ccagccgttc ctcagcatcc acaggtcacg ccacccccct tcctgtcacc    12120
gacacttcct cagtatccac aggtcacgcc acccctcttc ctgtcaccag cacttcctca    12180
gtatctacag gtcacgccac ccctcttcct gtcaccagcc cttcctcagc atccacaggt    12240
cacgccaccc ctgttcctgt caccagcact tcctcagcat ccaggtga caccacccct      12300 cttcctgtca ccaatgcttc ctcattatcc acaggtcacg ccaccctct tcatgtcacc     12360 agcccttcct cagcatccag aggtgacacc agcactcttc ctgtcaccga tgcttcctca    12420
gcatccaccg gtcacgccac ccctcttcct ctcaccagcc tttcctcagt atccacaggt    12480
gacaccacgc ctcttcctgt caccgacact tcctctgcat ccaggtca ggccacccct      12540 cttcctgtca ccagccttc ctcagtatcc acaggtgaca ccacgcctct tcctgtcacc     12600
atcccttcct cagcatcctc aggtcacacc acctctcttc ctgtcaccga cgcttcctca    12660
gtgtccacag gtcacggcac ccctcttcct gtcaccagca cttcctcagc atccacaggt    12720
gacaccaccc ctcttcctgt caccgacact tcctcagcat ccaggtca cgccacccct      12780 cttcctgtca ccgacacttc ctcagcatcc acaggtcacg ccaccctct tcctgtcacc     12840 agcctttcct cagtatccac aggtcacgcc acccctcttg ctgtcagcag tgctacctca    12900
gcttccacag tatcctcgga ctcccctctg aagatggaaa caccaggaat gacaacaccg    12960
tcactgaaga cagacggtgg gagacgcaca gccacatcac cacccccac aacctcccag     13020 accatcattt ccaccattcc cagcactgcc atgcacaccc gctccacagc tgccccatc     13080 cccatcctgc ctgagagagg agtttccctc ttccccattg ggcaggcgc cggggacctg    13140 gagttcgtca ggaggaccgt ggacttcacc tccccactct tcaagccggc gactggcttc    13200 cccccttggct cctctctccg tgattcctc tacttcacag acaatggcca gatcatcttc     13260
ccagagtcag actaccagat tttctcctac cccaacccac tcccaacagg cttcacaggc    13320
cgggaccctg tggccctggt ggctccgttc tgggacgatg ctgacttctc cactggtcgg    13380
gggaccacat tttatcagga atacgagacg ttctatggtg aacacagcct gctagtccag    13440
caggccgagt cttggattag aaagatgaca acaacggggg gctacaaggc caggtgggcc    13500
ctaaaggtca cgtgggtcaa tgcccacgcc tatcctgccc agtggaccct cgggagcaac    13560
acctaccaag ccatcctctc cacggacggg agcaggtcct atgccctgtt tctctaccag    13620
agcggtggga tgcagtggga cgtggcccag cgctcaggca acccggtgct catgggcttc    13680
tctagtggag atggctattt cgaaaacagc ccactgatgt cccagccagt gtgggagagg    13740
tatcgccctg atagattcct gaattccaac tcaggcctcc aagggctgca gttctacagg    13800
ctacaccggg aagaaaggcc caactaccgt ctcgagtgcc tgcagtggct gaagagccag    13860
cctcggtggc ccagctgggg ctggaaccag gtctcctgcc cttgttcctg gcagcaggga    13920
```

-continued

```
cgacgggact tacgattcca acccgtcagc ataggtcgct ggggcctcgg cagtaggcag    13980
ctgtgcagct tcacctcttg gcgaggaggc gtgtgctgca gctacgggcc ctggggagag    14040
tttcgtgaag gctggcacgt gcagcgtcct tggcagttgg cccaggaact ggagccacag    14100
agctggtgct gccgctggaa tgacaagccc tacctctgtg ccctgtacca gcagaggcgg    14160
ccccacgtgg gctgtgctac atacaggccc ccacagcccg cctggatgtt cggggacccc    14220
cacatcacca ccttggatgg tgtcagttac accttcaatg ggctgggggA cttcctgctg    14280
gtcgggGccc aagacgggaa ctcctccttc ctgcttcagg gccgcaccgc ccagactggc    14340
tcagcccagg ccaccaactt catcgccttt gcggctcagt accgctccag cagcctgggc    14400
cccgtcacgg tccaatggct ccttgagcct cacgacgcaa tccgtgtcct gctggataac    14460
cagactgtga catttcagcc tgaccatgaa gacggcggag gccaggagac gttcaacgcc    14520
accggagtcc tcctgagccg caacggctct gaggtctcgg ccagcttcga cggctgggcc    14580
accgtctcgg tgatcgcgct ctccaacatc ctccacgcct ccgccagcct cccgcccgag    14640
taccagaacc gcacggaggg gctcctgggg gtctggaata acaatccaga ggacgacttc    14700
aggatgccca atggctccac cattccccca gggagccctg aggagatgct tttccacttt    14760
ggaatgacct ggcagatcaa cgggacaggc ctccttggca agaggaatga ccagctgcct    14820
tccaacttca cccctgtttt ctactcacaa ctgcaaaaaa acagctcctg ggctgaacat    14880
ttgatctcca actgtgacgg agatagctca tgcatctatg acaccctggc cctgcgcaac    14940
gcaagcatcg gacttcacac gagggaagtc agtaaaaaac tacgagcaggc gaacgccacc    15000
ctcaatcagt acccgccctc catcaatggt ggtcgtgtga ttgaagccta caaggggcag    15060
accacgctga ttcagtacac cagcaatgct gaggatgcca acttcacgct cagagacagc    15120
tgcaccgact tggagctctt tgagaatggg acgttgctgt ggacacccaa gtcgctggag    15180
ccattcactc tggagattct agcaagaagt gccaagattg gcttggcatc tgcactccag    15240
cccaggactg tggtctgcca ttgcaatgca gagagccagt gtttgtacaa tcagaccagc    15300
agggtgggca actcctccct ggaggtggct ggctgcaagt gtgacggggg caccttcggc    15360
cgctactgcg agggctccga ggatgcctgt gaggagccgt gcttcccgag tgtccactgc    15420
gttcctggga agggctgcga ggcctgccct ccaaacctga ctggggatgg gcggcactgt    15480
gcggctctgg ggagctcttt cctgtgtcag aaccagtcct gccctgtgaa ttactgctac    15540
aatcaaggcc actgctacat ctcccagact ctgggctgtc agcccatgtg cacctgcccc    15600
ccagccttca ctgacagccg ctgcttcctg gctgggaaca acttcagtcc aactgtcaac    15660
ctagaacttc ccttaagagt catccagctc ttgctcagtg aagaggaaaa tgcctccatg    15720
gcagaagtca acgcctcggt ggcatacaga ctggggaccc tggacatgcg ggcctttctc    15780
cgcaacagcc aagtggaacg aatcgattct gcagcaccgg cctcgggaag ccccatccaa    15840
cactggatgg tcatctcgga gttccagtac cgccctcggg gccggtcat tgacttcctg    15900
aacaaccagc tgctggccgc ggtggtggag gcgttcttat accacgttcc acggaggagt    15960
gaggagccca ggaacgacgt ggtcttccag cccatctccg gggaagacgt gcgcgatgtg    16020
acagccctga acgtgagcac gctgaaggct tacttcagat gcgatggcta caagggctac    16080
gacctggtct acagccccca gagcggcttc acctgcgtgt cccgtgcag tagggggctac    16140
tgtgaccatg gaggccagtg ccagcacctg ccagtgggc cccgctgcag ctgtgtgtcc    16200
ttctccatct acacggcctg gggcgagcac tgtgagcacc tgagcatgaa actcgacgcg    16260
ttcttcggca tcttctttgg ggccctgggc ggcctcttgc tgctgggggt cgggacgttc    16320
```

-continued

```
gtggtcctgc gcttctgggg ttgctccggg gccaggttct cctatttcct gaactcagct    16380
gaggccttgc cttgaagggg cagctgtggc ctaggctacc tcaagactca cctcatcctt    16440
accgcacatt taaggcgcca ttgcttttgg gagactggaa aagggaaggt gactgaaggc    16500
tgtcaggatt cttcaaggag aatgaatact gggaatcaag acaagactat accttatcca    16560
taggcgcagg tgcacagggg gaggccataa agatcaaaca tgcatggatg ggtcctcacg    16620
cagacacacc cacagaagga cactagcctg tgcacgcgcg cgtgcacaca cacacacaca    16680
cacacgagtt cataatgtgg tgatggccct aagttaagca aaatgcttct gcacacaaaa    16740
ctctctggtt tacttcaaat taactctatt taaataaagt ctctctgact ttttgtgtct    16800
ccaaaaaaaa aaaaaaaa                                                  16819
```

<210> SEQ ID NO 2
<211> LENGTH: 5412
<212> TYPE: PRT
<213> ORGANISM: Homo sapiens

<400> SEQUENCE: 2

```
Met Lys Gly Ala Arg Trp Arg Val Pro Trp Val Ser Leu Ser Cys
1               5                   10                  15

Leu Cys Leu Cys Leu Leu Pro His Val Val Pro Gly Thr Thr Glu Asp
                20                  25                  30

Thr Leu Ile Thr Gly Ser Lys Thr Ala Ala Pro Val Thr Ser Thr Gly
                35                  40                  45

Ser Thr Thr Ala Thr Leu Glu Gly Gln Ser Thr Ala Ala Ser Ser Arg
            50                  55                  60

Thr Ser Asn Gln Asp Ile Ser Ala Ser Ser Gln Asn His Gln Thr Lys
65              70                  75                  80

Ser Thr Glu Thr Thr Ser Lys Ala Gln Thr Asp Thr Leu Thr Gln Met
                85                  90                  95

Met Thr Ser Thr Leu Phe Ser Ser Pro Ser Val His Asn Val Met Glu
            100                 105                 110

Thr Ala Pro Pro Asp Glu Met Thr Thr Ser Phe Pro Ser Ser Val Thr
        115                 120                 125

Asn Thr Leu Met Met Thr Ser Lys Thr Ile Thr Met Thr Thr Ser Thr
    130                 135                 140

Asp Ser Thr Leu Gly Asn Thr Glu Glu Thr Ser Thr Ala Gly Thr Glu
145                 150                 155                 160

Ser Ser Thr Pro Val Thr Ser Ala Val Ser Ile Thr Ala Gly Gln Glu
                165                 170                 175

Gly Gln Ser Arg Thr Thr Ser Trp Arg Thr Ser Ile Gln Asp Thr Ser
            180                 185                 190

Ala Ser Ser Gln Asn His Trp Thr Arg Ser Thr Gln Thr Thr Arg Glu
        195                 200                 205

Ser Gln Thr Ser Thr Leu Thr His Arg Thr Thr Ser Thr Pro Ser Phe
    210                 215                 220

Ser Pro Ser Val His Asn Val Thr Gly Thr Val Ser Gln Lys Thr Ser
225                 230                 235                 240

Pro Ser Gly Glu Thr Ala Thr Ser Ser Leu Cys Ser Val Thr Asn Thr
                245                 250                 255

Ser Met Met Thr Ser Glu Lys Ile Thr Val Thr Thr Ser Thr Gly Ser
            260                 265                 270

Thr Leu Gly Asn Pro Gly Glu Thr Ser Ser Val Pro Thr Gly Ser
        275                 280                 285
```

```
Leu Met Pro Val Thr Ser Ala Ala Leu Val Thr Phe Asp Pro Glu Gly
    290                 295                 300

Gln Ser Pro Ala Thr Phe Ser Arg Thr Ser Thr Gln Asp Thr Thr Ala
305                 310                 315                 320

Phe Ser Lys Asn His Gln Thr Gln Ser Val Glu Thr Thr Arg Val Ser
                325                 330                 335

Gln Ile Asn Thr Leu Asn Thr Leu Thr Pro Val Thr Thr Ser Thr Val
            340                 345                 350

Leu Ser Ser Pro Ser Gly Phe Asn Pro Ser Gly Thr Val Ser Gln Glu
        355                 360                 365

Thr Phe Pro Ser Gly Glu Thr Thr Thr Ser Ser Pro Ser Ser Val Ser
370                 375                 380

Asn Thr Phe Leu Val Thr Ser Lys Val Phe Arg Met Pro Thr Ser Arg
385                 390                 395                 400

Asp Ser Thr Leu Gly Asn Thr Glu Glu Thr Ser Leu Ser Val Ser Gly
                405                 410                 415

Thr Ile Ser Ala Ile Thr Ser Lys Val Ser Thr Ile Trp Trp Ser Asp
            420                 425                 430

Thr Leu Ser Thr Ala Leu Ser Pro Ser Ser Leu Pro Pro Lys Ile Ser
        435                 440                 445

Thr Ala Phe His Thr Gln Gln Ser Glu Gly Ala Glu Thr Thr Gly Arg
450                 455                 460

Pro His Glu Arg Ser Ser Phe Ser Pro Gly Val Ser Gln Glu Ile Phe
465                 470                 475                 480

Thr Leu His Glu Thr Thr Thr Trp Pro Ser Ser Phe Ser Ser Lys Gly
                485                 490                 495

His Thr Thr Trp Ser Gln Thr Glu Leu Pro Ser Thr Ser Thr Gly Ala
            500                 505                 510

Ala Thr Arg Leu Val Thr Gly Asn Pro Ser Thr Gly Thr Ala Gly Thr
        515                 520                 525

Ile Pro Arg Val Pro Ser Lys Val Ser Ala Ile Gly Glu Pro Gly Glu
530                 535                 540

Pro Thr Thr Tyr Ser Ser His Ser Thr Thr Leu Pro Lys Thr Thr Gly
545                 550                 555                 560

Ala Gly Ala Gln Thr Gln Trp Thr Gln Glu Thr Gly Thr Thr Gly Glu
                565                 570                 575

Ala Leu Leu Ser Ser Pro Ser Tyr Ser Val Thr Gln Met Ile Lys Thr
            580                 585                 590

Ala Thr Ser Pro Ser Ser Ser Pro Met Leu Asp Arg His Thr Ser Gln
        595                 600                 605

Gln Ile Thr Thr Ala Pro Ser Thr Asn His Ser Thr Ile His Ser Thr
610                 615                 620

Ser Thr Ser Pro Gln Glu Ser Pro Ala Val Ser Gln Arg Gly His Thr
625                 630                 635                 640

Gln Ala Pro Gln Thr Thr Gln Glu Ser Gln Thr Thr Arg Ser Val Ser
                645                 650                 655

Pro Met Thr Asp Thr Lys Thr Val Thr Thr Pro Gly Ser Ser Phe Thr
            660                 665                 670

Ala Ser Gly His Ser Pro Ser Glu Ile Val Pro Gln Asp Ala Pro Thr
        675                 680                 685

Ile Ser Ala Ala Thr Thr Phe Ala Pro Ala Pro Thr Gly Asp Gly His
690                 695                 700
```

```
Thr Thr Gln Ala Pro Thr Ala Leu Gln Ala Pro Ser Ser His
705                 710                 715                 720

Asp Ala Thr Leu Gly Pro Ser Gly Thr Ser Leu Ser Lys Thr Gly
                725                 730                 735

Ala Leu Thr Leu Ala Asn Ser Val Val Ser Thr Pro Gly Pro Glu
                740                 745                 750

Gly Gln Trp Thr Ser Ala Ser Ala Ser Thr Ser Pro Asp Thr Ala Ala
                755                 760                 765

Ala Met Thr His Thr His Gln Ala Glu Ser Thr Glu Ala Ser Gly Gln
        770                 775                 780

Thr Gln Thr Ser Glu Pro Ala Ser Ser Gly Ser Arg Thr Thr Ser Ala
785                 790                 795                 800

Gly Thr Ala Thr Pro Ser Ser Ser Gly Ala Ser Gly Thr Thr Pro Ser
                805                 810                 815

Gly Ser Glu Gly Ile Ser Thr Ser Gly Glu Thr Thr Arg Phe Ser Ser
                820                 825                 830

Asn Pro Ser Arg Asp Ser His Thr Thr Gln Ser Thr Thr Glu Leu Leu
                835                 840                 845

Ser Ala Ser Ala Ser His Gly Ala Ile Pro Val Ser Thr Gly Met Ala
850                 855                 860

Ser Ser Ile Val Pro Gly Thr Phe His Pro Thr Leu Ser Glu Ala Ser
865                 870                 875                 880

Thr Ala Gly Arg Pro Thr Gly Gln Ser Ser Pro Thr Ser Pro Ser Ala
                885                 890                 895

Ser Pro Gln Glu Thr Ala Ala Ile Ser Arg Met Ala Gln Thr Gln Arg
                900                 905                 910

Thr Arg Thr Ser Arg Gly Ser Asp Thr Ile Ser Leu Ala Ser Gln Ala
                915                 920                 925

Thr Asp Thr Phe Ser Thr Val Pro Pro Thr Pro Pro Ser Ile Thr Ser
930                 935                 940

Thr Gly Leu Thr Ser Pro Gln Thr Glu Thr His Thr Leu Ser Pro Ser
945                 950                 955                 960

Gly Ser Gly Lys Thr Phe Thr Thr Ala Leu Ile Ser Asn Ala Thr Pro
                965                 970                 975

Leu Pro Val Thr Tyr Ala Ser Ser Ala Ser Thr Gly His Thr Thr Pro
                980                 985                 990

Leu His Val Thr Asp Ala Ser Ser Val Ser Thr Gly His Ala Thr Pro
                995                 1000                1005

Leu Pro Val Thr Ser Pro Ser Ser Val Ser Thr Gly His Thr Thr
1010                1015                1020

Pro Leu Pro Val Thr Asp Thr Ser Ser Glu Ser Thr Gly His Val
                1025                1030                1035

Thr Pro Leu Pro Val Thr Ser Phe Ser Ser Ala Ser Thr Gly Asp
            1040                1045                1050

Ser Thr Pro Leu Pro Val Thr Asp Thr Ser Ser Ala Ser Thr Gly
    1055                1060                1065

His Val Thr Pro Leu Pro Val Thr Ser Leu Ser Ser Ala Ser Thr
    1070                1075                1080

Gly Asp Thr Thr Pro Leu Pro Val Thr Asp Thr Ser Ser Ala Ser
        1085                1090                1095

Thr Gly His Ala Thr Ser Leu Pro Val Thr Asp Thr Ser Ser Val
    1100                1105                1110
```

```
Ser Thr Gly His Thr Thr Pro Leu Pro Val Thr Asp Thr Ser Ser
    1115                1120                1125

Ala Ser Thr Gly His Ala Thr Ser Leu Pro Val Thr Asp Thr Ser
    1130                1135                1140

Ser Val Ser Thr Gly His Thr Thr Pro Leu His Val Thr Asp Ala
    1145                1150                1155

Ser Ser Ala Ser Thr Gly Gln Ala Thr Pro Leu Pro Val Thr Ser
    1160                1165                1170

Leu Ser Ser Val Ser Thr Gly Asp Thr Thr Pro Leu Pro Val Thr
    1175                1180                1185

Ser Pro Ser Ser Ala Ser Thr Gly His Ala Thr Pro Leu Leu Val
    1190                1195                1200

Thr Asp Thr Ser Ser Ala Ser Thr Gly His Ala Thr Pro Leu Pro
    1205                1210                1215

Val Thr Asp Ala Ser Ser Val Ser Thr Asp His Ala Thr Ser Leu
    1220                1225                1230

Pro Val Thr Ile Pro Ser Ala Ala Ser Thr Gly His Thr Thr Pro
    1235                1240                1245

Leu Pro Val Thr Asp Thr Ser Ser Ala Ser Thr Gly Gln Ala Thr
    1250                1255                1260

Ser Leu Leu Val Thr Asp Thr Ser Ser Val Ser Thr Gly Asp Thr
    1265                1270                1275

Thr Pro Leu Pro Val Thr Ser Thr Ser Ser Ala Ser Thr Gly His
    1280                1285                1290

Val Thr Pro Leu His Val Thr Ser Pro Ser Ser Ala Ser Thr Gly
    1295                1300                1305

His Ala Thr Pro Leu Pro Val Thr Ser Leu Ser Ser Ala Ser Thr
    1310                1315                1320

Gly Asp Thr Met Pro Leu Pro Val Thr Ser Pro Ser Ser Ala Ser
    1325                1330                1335

Thr Gly Asp Thr Thr Pro Leu Pro Val Thr Asp Ala Ser Ser Val
    1340                1345                1350

Ser Thr Gly His Thr Thr Pro Leu His Val Thr Asp Ala Ser Ser
    1355                1360                1365

Ala Ser Thr Gly Gln Ala Thr Pro Leu Pro Val Thr Ser Leu Ser
    1370                1375                1380

Ser Val Ser Thr Gly Asp Thr Thr Pro Leu Pro Val Thr Ser Pro
    1385                1390                1395

Ser Ser Ala Ser Thr Gly His Ala Thr Pro Leu Leu Val Thr Asp
    1400                1405                1410

Thr Ser Ser Ala Ser Thr Gly His Ala Thr Pro Leu Pro Val Thr
    1415                1420                1425

Asp Ala Ser Ser Val Ser Thr Asp His Ala Thr Ser Leu Pro Val
    1430                1435                1440

Thr Ile Pro Ser Ala Ala Ser Thr Gly His Thr Thr Pro Leu Pro
    1445                1450                1455

Val Thr Asp Thr Ser Ser Ala Ser Thr Gly Gln Ala Thr Ser Leu
    1460                1465                1470

Leu Val Thr Asp Thr Ser Ser Val Ser Thr Gly Asp Thr Thr Pro
    1475                1480                1485

Leu Pro Val Thr Ser Thr Ser Ser Ala Ser Thr Gly His Val Thr
    1490                1495                1500
```

```
Pro Leu His Val Thr Ser Pro Ser Ser Ala Ser Thr Gly His Ala
    1505                1510                1515

Thr Pro Leu Pro Val Thr Ser Leu Ser Ser Ala Ser Thr Gly Asp
    1520                1525                1530

Thr Met Pro Leu Pro Val Thr Ser Pro Ser Ser Ala Ser Thr Gly
    1535                1540                1545

Asp Thr Thr Pro Leu Pro Val Thr Asp Ala Ser Ser Val Ser Thr
    1550                1555                1560

Gly His Thr Thr Pro Leu Pro Val Thr Ser Pro Ser Ser Ala Ser
    1565                1570                1575

Thr Gly His Thr Thr Pro Leu Pro Val Thr Asp Thr Ser Ser Ala
    1580                1585                1590

Ser Lys Gly Asp Thr Thr Pro Leu Pro Val Thr Ser Pro Ser Ser
    1595                1600                1605

Ala Ser Thr Gly His Thr Thr Pro Leu Pro Val Thr Asp Thr Ser
    1610                1615                1620

Ser Ala Ser Thr Gly Asp Thr Thr Pro Leu Pro Val Thr Asn Ala
    1625                1630                1635

Ser Ser Leu Ser Thr Gly His Ala Thr Pro Leu His Val Thr Ser
    1640                1645                1650

Pro Ser Ser Ala Ser Thr Gly His Ala Thr Pro Leu Pro Val Thr
    1655                1660                1665

Ser Thr Ser Ser Ala Ser Thr Gly His Ala Thr Pro Leu Pro Val
    1670                1675                1680

Thr Gly Leu Ser Ser Ala Thr Thr Asp Asp Thr Thr Arg Leu Pro
    1685                1690                1695

Val Thr Asp Val Ser Ser Ala Ser Thr Gly Gln Ala Thr Pro Leu
    1700                1705                1710

Pro Val Thr Ser Leu Ser Ser Val Ser Thr Gly Asp Thr Thr Pro
    1715                1720                1725

Leu Pro Val Thr Ser Pro Ser Ser Ala Ser Thr Gly His Ala Ser
    1730                1735                1740

Pro Leu Leu Val Thr Asp Ala Ser Ser Ala Ser Thr Gly Gln Ala
    1745                1750                1755

Thr Pro Leu Pro Val Thr Asp Thr Ser Ser Val Ser Thr Ala His
    1760                1765                1770

Ala Thr Pro Leu Pro Val Thr Gly Leu Ser Ser Ala Ser Thr Asp
    1775                1780                1785

Asp Thr Thr Arg Leu Pro Val Thr Asp Val Ser Ser Ala Ser Thr
    1790                1795                1800

Gly Gln Ala Ile Pro Leu Pro Val Thr Ser Pro Ser Ser Ala Ser
    1805                1810                1815

Thr Gly Asp Thr Thr Pro Leu Pro Val Thr Asp Ala Ser Ser Ala
    1820                1825                1830

Ser Thr Gly Asp Thr Thr Ser Leu Pro Val Thr Ile Pro Ser Ser
    1835                1840                1845

Ala Ser Ser Gly His Thr Thr Ser Leu Pro Val Thr Asp Ala Ser
    1850                1855                1860

Ser Val Ser Thr Gly His Ala Thr Ser Leu Leu Val Thr Asp Ala
    1865                1870                1875

Ser Ser Val Ser Thr Gly Asp Thr Thr Pro Leu Pro Val Thr Asp
    1880                1885                1890
```

-continued

```
Thr Asn Ser Ala Ser Thr Gly Asp Thr Thr Pro Leu His Val Thr
    1895                1900            1905
Asp Ala Ser Ser Val Ser Thr Gly His Ala Thr Ser Leu Pro Val
    1910                1915            1920
Thr Ser Leu Ser Ser Ala Ser Thr Gly Asp Thr Thr Pro Leu Pro
    1925                1930            1935
Val Thr Ser Pro Ser Ser Ala Ser Ser Gly His Thr Thr Pro Leu
    1940                1945            1950
Pro Val Thr Asp Ala Ser Ser Val Pro Thr Gly His Ala Thr Ser
    1955                1960            1965
Leu Pro Val Thr Asp Ala Ser Ser Val Ser Thr Gly His Ala Thr
    1970                1975            1980
Pro Leu Pro Val Thr Asp Ala Ser Ser Val Ser Thr Gly His Ala
    1985                1990            1995
Thr Pro Leu Pro Val Thr Asp Thr Ser Ser Val Ser Thr Gly Gln
    2000                2005            2010
Ala Thr Pro Leu Pro Val Thr Ser Leu Ser Ser Ala Ser Thr Gly
    2015                2020            2025
Asp Thr Thr Pro Leu Pro Val Thr Asp Thr Ser Ser Ala Ser Thr
    2030                2035            2040
Gly Gln Asp Thr Pro Leu Pro Val Thr Ser Leu Ser Ser Val Ser
    2045                2050            2055
Thr Gly Asp Thr Thr Pro Leu Pro Val Thr Asn Pro Ser Ser Ala
    2060                2065            2070
Ser Thr Gly His Ala Thr Pro Leu Leu Val Thr Asp Ala Ser Ser
    2075                2080            2085
Ile Ser Thr Gly His Ala Thr Ser Leu Leu Val Thr Asp Ala Ser
    2090                2095            2100
Ser Val Ser Thr Gly His Ala Thr Ala Leu His Asp Thr Asp Ala
    2105                2110            2115
Ser Ser Leu Ser Thr Gly Asp Thr Thr Pro Leu Pro Val Thr Ser
    2120                2125            2130
Pro Ser Ser Thr Ser Thr Gly Asp Thr Thr Pro Leu Pro Val Thr
    2135                2140            2145
Glu Thr Ser Ser Val Ser Thr Gly His Ala Thr Ser Leu Pro Val
    2150                2155            2160
Thr Asp Thr Ser Ser Ala Ser Thr Gly His Ala Thr Ser Leu Pro
    2165                2170            2175
Val Thr Asp Thr Ser Ser Ala Ser Thr Gly His Ala Thr Pro Leu
    2180                2185            2190
Pro Val Thr Asp Thr Ser Ser Ala Ser Thr Gly Gln Ala Thr Pro
    2195                2200            2205
Leu Pro Val Thr Ser Pro Ser Ala Ser Thr Gly His Ala Ile
    2210                2215            2220
Pro Leu Leu Val Thr Asp Thr Ser Ser Ala Ser Thr Gly Gln Ala
    2225                2230            2235
Thr Pro Leu Pro Val Thr Ser Leu Ser Ser Ala Ser Thr Gly Asp
    2240                2245            2250
Thr Thr Pro Leu Pro Val Thr Asp Ala Ser Ser Val Ser Thr Gly
    2255                2260            2265
His Ala Thr Ser Leu Pro Val Thr Ser Leu Ser Ser Val Ser Thr
    2270                2275            2280
```

```
Gly Asp Thr Thr Pro Leu Pro Val Thr Ser Pro Ser Ser Ala Ser
    2285                2290                2295

Thr Gly His Ala Thr Pro Leu His Val Thr Asp Ala Ser Ser Ala
    2300                2305                2310

Ser Thr Gly His Ala Thr Pro Leu Pro Val Thr Ser Leu Ser Ser
    2315                2320                2325

Ala Ser Thr Gly Asp Thr Thr Pro Leu Pro Val Thr Ser Pro Ser
    2330                2335                2340

Ser Ala Ser Thr Gly His Ala Thr Pro Leu His Val Thr Asp Ala
    2345                2350                2355

Ser Ser Val Ser Thr Gly Asp Thr Thr Pro Leu Pro Val Thr Ser
    2360                2365                2370

Ser Ser Ser Ala Ser Ser Gly His Thr Thr Pro Leu Pro Val Thr
    2375                2380                2385

Asp Ala Ser Ser Ala Ser Thr Gly Asp Thr Thr Pro Leu Pro Val
    2390                2395                2400

Thr Asp Thr Ser Ser Ala Ser Thr Gly His Ala Thr His Leu Pro
    2405                2410                2415

Val Thr Gly Leu Ser Ser Ala Ser Thr Gly Asp Thr Thr Arg Leu
    2420                2425                2430

Pro Val Thr Asn Val Ser Ser Ala Ser Thr Gly His Ala Thr Pro
    2435                2440                2445

Leu Pro Val Thr Ser Thr Ser Ser Ala Ser Thr Gly Asp Thr Thr
    2450                2455                2460

Pro Leu Pro Gly Thr Asp Thr Ser Ser Val Ser Thr Gly His Thr
    2465                2470                2475

Thr Pro Leu Leu Val Thr Asp Ala Ser Ser Val Ser Thr Gly Asp
    2480                2485                2490

Thr Thr Arg Leu Pro Val Thr Ser Pro Ser Ser Ala Ser Thr Gly
    2495                2500                2505

His Thr Thr Pro Leu Pro Val Thr Asp Thr Pro Ser Ala Ser Thr
    2510                2515                2520

Gly Asp Thr Thr Pro Leu Pro Val Thr Asn Ala Ser Ser Leu Ser
    2525                2530                2535

Thr Arg His Ala Thr Ser Leu His Val Thr Ser Pro Ser Ser Ala
    2540                2545                2550

Ser Thr Gly His Ala Thr Ser Leu Pro Val Thr Asp Thr Ser Ala
    2555                2560                2565

Ala Ser Thr Gly His Ala Thr Pro Leu Pro Val Thr Ser Thr Ser
    2570                2575                2580

Ser Ala Ser Thr Gly Asp Thr Thr Pro Leu Pro Val Thr Asp Thr
    2585                2590                2595

Tyr Ser Ala Ser Thr Gly Gln Ala Thr Pro Leu Pro Val Thr Ser
    2600                2605                2610

Leu Ser Ser Val Ser Thr Gly Asp Thr Thr Pro Leu Pro Val Thr
    2615                2620                2625

Ser Pro Ser Ser Ala Ser Thr Gly His Ala Thr Pro Leu Leu Val
    2630                2635                2640

Thr Asp Ala Ser Ser Ala Ser Thr Gly Gln Ala Thr Pro Leu Pro
    2645                2650                2655

Val Thr Ser Leu Ser Ser Val Ser Thr Gly Asp Thr Thr Pro Leu
    2660                2665                2670
```

-continued

```
Pro Val Thr Ser Pro Ser Ser Ala Ser Thr Gly His Ala Thr Ser
    2675                2680                2685

Leu Pro Val Thr Asp Thr Ser Ser Ala Ser Thr Gly Asp Thr Thr
    2690                2695                2700

Ser Leu Pro Val Thr Asp Thr Ser Ser Ala Tyr Thr Gly Asp Thr
    2705                2710                2715

Thr Ser Leu Pro Val Thr Asp Thr Ser Ser Ser Thr Gly Asp
    2720                2725                2730

Thr Thr Pro Leu Leu Val Thr Glu Thr Ser Ser Val Ser Thr Gly
    2735                2740                2745

Asp Thr Thr Pro Leu Pro Val Thr Asp Thr Ser Ser Ala Ser Thr
    2750                2755                2760

Gly His Ala Thr Pro Leu Pro Val Thr Asn Thr Ser Ser Val Ser
    2765                2770                2775

Thr Gly His Ala Thr Pro Leu His Val Thr Ser Pro Ser Ser Ala
    2780                2785                2790

Ser Thr Gly His Thr Thr Pro Leu Pro Val Thr Asp Ala Ser Ser
    2795                2800                2805

Val Ser Thr Gly His Ala Thr Ser Leu Pro Val Thr Asp Ala Ser
    2810                2815                2820

Ser Val Phe Thr Gly His Ala Thr Ser Leu Pro Val Thr Ile Pro
    2825                2830                2835

Ser Ser Ala Ser Ser Gly His Thr Thr Pro Leu Pro Val Thr Asp
    2840                2845                2850

Ala Ser Ser Val Ser Thr Gly His Ala Thr Ser Leu Pro Val Thr
    2855                2860                2865

Asp Ala Ser Ser Val Ser Thr Gly His Ala Thr Pro Leu Pro Val
    2870                2875                2880

Thr Asp Ala Ser Ser Val Ser Thr Gly His Ala Thr Pro Leu Pro
    2885                2890                2895

Leu Thr Ser Leu Ser Ser Val Ser Thr Gly Asp Thr Thr Pro Leu
    2900                2905                2910

Pro Val Thr Asp Thr Ser Ser Ala Ser Thr Gly Gln Ala Thr Pro
    2915                2920                2925

Leu Pro Val Thr Ser Leu Ser Ser Val Ser Thr Gly Asp Thr Thr
    2930                2935                2940

Pro Leu Pro Val Thr Asp Thr Ser Ser Ala Ser Thr Gly His Ala
    2945                2950                2955

Thr Ser Leu Pro Val Thr Asp Thr Ser Ser Ala Ser Thr Gly His
    2960                2965                2970

Ala Thr Pro Leu Pro Asp Thr Asp Ser Ser Ala Ser Thr Gly
    2975                2980                2985

His Ala Thr Leu Leu Pro Val Thr Asp Thr Ser Ser Ala Ser Ile
    2990                2995                3000

Gly His Ala Thr Ser Leu Pro Val Thr Asp Thr Ser Ser Ile Ser
    3005                3010                3015

Thr Gly His Ala Thr Pro Leu His Val Thr Ser Pro Ser Ser Ala
    3020                3025                3030

Ser Thr Gly His Ala Thr Pro Leu Pro Val Thr Asp Thr Ser Ser
    3035                3040                3045

Ala Ser Thr Gly His Ala Asn Pro Leu His Val Thr Ser Pro Ser
    3050                3055                3060
```

-continued

```
Ser Ala Ser Thr Gly His Ala Thr Pro Leu Pro Val Thr Asp Thr
3065                3070                3075

Ser Ser Ala Ser Thr Gly His Ala Thr Pro Leu Pro Val Thr Ser
3080                3085                3090

Leu Ser Ser Val Ser Thr Gly Asp Thr Thr Pro Leu Pro Val Thr
3095                3100                3105

Ser Pro Ser Ser Ala Ser Thr Gly His Thr Thr Pro Leu Pro Val
3110                3115                3120

Thr Asp Thr Ser Ser Ala Ser Thr Gly Gln Ala Thr Ala Leu Pro
3125                3130                3135

Val Thr Ser Thr Ser Ser Ala Ser Thr Gly Asp Thr Thr Pro Leu
3140                3145                3150

Pro Val Thr Asp Thr Ser Ser Ala Ser Thr Gly Gln Ala Thr Pro
3155                3160                3165

Leu Pro Val Thr Ser Leu Ser Ser Val Ser Thr Gly Asp Thr Thr
3170                3175                3180

Pro Leu Pro Val Thr Ser Pro Ser Ser Ala Ser Thr Gly His Ala
3185                3190                3195

Thr Pro Leu Leu Val Thr Asp Ala Ser Ser Ala Ser Thr Gly Gln
3200                3205                3210

Ala Thr Pro Leu Pro Val Thr Ser Leu Ser Ser Val Ser Thr Gly
3215                3220                3225

Asp Thr Thr Pro Leu Pro Val Thr Ser Pro Ser Ser Ala Ser Thr
3230                3235                3240

Gly His Ala Thr Ser Leu Pro Val Thr Asp Thr Ser Ser Ala Ser
3245                3250                3255

Thr Gly Asp Thr Thr Ser Leu Pro Val Thr Asp Thr Ser Ser Ala
3260                3265                3270

Tyr Thr Gly Asp Thr Thr Ser Leu Pro Val Thr Asp Thr Ser Ser
3275                3280                3285

Ser Ser Thr Gly Asp Thr Thr Pro Leu Leu Val Thr Glu Thr Ser
3290                3295                3300

Ser Val Ser Thr Gly His Ala Thr Pro Leu Leu Val Thr Asp Ala
3305                3310                3315

Ser Ser Ala Ser Thr Gly His Ala Thr Pro Leu His Val Thr Ser
3320                3325                3330

Pro Ser Ser Ala Ser Thr Gly Asp Thr Thr Pro Val Pro Val Thr
3335                3340                3345

Asp Thr Ser Ser Val Ser Thr Gly His Ala Thr Pro Leu Pro Val
3350                3355                3360

Thr Gly Leu Ser Ser Ala Ser Thr Gly Asp Thr Thr Arg Leu Pro
3365                3370                3375

Val Thr Asp Ile Ser Ser Ala Ser Thr Gly Gln Ala Thr Pro Leu
3380                3385                3390

Pro Val Thr Asn Thr Ser Ser Val Ser Thr Gly Asp Thr Met Pro
3395                3400                3405

Leu Pro Val Thr Ser Pro Ser Ser Ala Ser Thr Gly His Ala Thr
3410                3415                3420

Pro Leu Pro Val Thr Ser Ser Ser Ala Ser Thr Gly His Ala
3425                3430                3435

Thr Pro Val Pro Val Thr Ser Thr Ser Ser Ala Ser Thr Gly His
3440                3445                3450
```

```
Thr Thr Pro Leu Pro Val Thr Asp Thr Ser Ser Ala Ser Thr Gly
    3455            3460                3465

Asp Thr Thr Pro Leu Pro Val Thr Ser Pro Ser Ser Ala Ser Thr
    3470            3475                3480

Gly His Thr Thr Pro Leu His Val Thr Ile Pro Ser Ser Ala Ser
    3485            3490                3495

Thr Gly Asp Thr Ser Thr Leu Pro Val Thr Gly Ala Ser Ser Ala
    3500            3505                3510

Ser Thr Gly His Ala Thr Pro Leu Pro Val Thr Asp Thr Ser Ser
    3515            3520                3525

Val Ser Thr Gly His Ala Thr Pro Leu Pro Val Thr Ser Leu Ser
    3530            3535                3540

Ser Val Ser Thr Gly Asp Thr Thr Pro Leu Pro Val Thr Asp Ala
    3545            3550                3555

Ser Ser Ala Ser Thr Gly Gln Ala Thr Pro Leu Pro Val Thr Ser
    3560            3565                3570

Leu Ser Ser Val Ser Thr Gly Asp Thr Thr Pro Leu Leu Val Thr
    3575            3580                3585

Asp Ala Ser Ser Val Ser Thr Gly His Ala Thr Pro Leu Pro Val
    3590            3595                3600

Thr Asp Thr Ser Ser Ala Ser Thr Gly Asp Thr Thr Arg Leu Pro
    3605            3610                3615

Val Thr Asp Thr Ser Ser Ala Ser Thr Gly Gln Ala Thr Pro Leu
    3620            3625                3630

Pro Val Thr Ser Leu Ser Ser Val Ser Thr Gly Asp Thr Thr Pro
    3635            3640                3645

Leu Leu Val Thr Asp Ala Ser Ser Val Ser Thr Gly His Ala Thr
    3650            3655                3660

Pro Leu Pro Val Thr Asp Thr Ser Ser Ala Ser Thr Gly Asp Thr
    3665            3670                3675

Thr Arg Leu Pro Val Thr Asp Thr Ser Ser Ala Ser Thr Gly Gln
    3680            3685                3690

Ala Thr Pro Leu Pro Val Thr Ile Pro Ser Ser Ser Ser Ser Gly
    3695            3700                3705

His Thr Thr Pro Leu Pro Val Thr Ser Thr Ser Ser Val Ser Thr
    3710            3715                3720

Gly His Val Thr Pro Leu His Val Thr Ser Pro Ser Ser Ala Ser
    3725            3730                3735

Thr Gly His Val Thr Pro Leu Pro Val Thr Ser Thr Ser Ser Ala
    3740            3745                3750

Ser Thr Gly His Ala Thr Pro Leu Leu Val Thr Asp Ala Ser Ser
    3755            3760                3765

Val Ser Thr Gly His Ala Thr Pro Leu Pro Val Thr Asp Ala Ser
    3770            3775                3780

Ser Ala Ser Thr Gly Asp Thr Thr Pro Leu Pro Val Thr Asp Thr
    3785            3790                3795

Ser Ser Ala Ser Thr Gly Gln Ala Thr Pro Leu Pro Val Thr Ser
    3800            3805                3810

Leu Ser Ser Val Ser Thr Gly Asp Thr Thr Pro Leu Pro Val Thr
    3815            3820                3825

Asp Ala Ser Ser Ala Ser Thr Gly His Ala Thr Pro Leu Pro Val
    3830            3835                3840
```

-continued

```
Thr Ile Pro Ser Ser Val Ser Thr Gly Asp Thr Met Pro Leu Pro
3845                3850                3855

Val Thr Ser Pro Ser Ser Ala Ser Thr Gly His Ala Thr Pro Leu
3860                3865                3870

Pro Val Thr Gly Leu Ser Ser Ala Ser Thr Gly Asp Thr Thr Pro
3875                3880                3885

Leu Pro Val Thr Asp Thr Ser Ser Ala Ser Thr Arg His Ala Thr
3890                3895                3900

Pro Leu Pro Val Thr Asp Thr Ser Ser Ala Ser Thr Asp Asp Thr
3905                3910                3915

Thr Arg Leu Pro Val Thr Asp Val Ser Ser Ala Ser Thr Gly His
3920                3925                3930

Ala Thr Pro Leu Pro Val Thr Ser Thr Ser Ser Ala Ser Thr Gly
3935                3940                3945

Asp Thr Thr Pro Leu Pro Val Thr Asp Thr Ser Ser Val Ser Thr
3950                3955                3960

Gly His Ala Thr Ser Leu Pro Val Thr Ser Arg Ser Ser Ala Ser
3965                3970                3975

Thr Gly His Ala Thr Pro Leu Pro Val Thr Asp Thr Ser Ser Val
3980                3985                3990

Ser Thr Gly His Ala Thr Pro Leu Pro Val Thr Ser Thr Ser Ser
3995                4000                4005

Val Ser Thr Gly His Ala Thr Pro Leu Pro Val Thr Ser Pro Ser
4010                4015                4020

Ser Ala Ser Thr Gly His Ala Thr Pro Val Pro Val Thr Ser Thr
4025                4030                4035

Ser Ser Ala Ser Thr Gly Asp Thr Thr Pro Leu Pro Val Thr Asn
4040                4045                4050

Ala Ser Ser Leu Ser Thr Gly His Ala Thr Pro Leu His Val Thr
4055                4060                4065

Ser Pro Ser Ser Ala Ser Arg Gly Asp Thr Ser Thr Leu Pro Val
4070                4075                4080

Thr Asp Ala Ser Ser Ala Ser Thr Gly His Ala Thr Pro Leu Pro
4085                4090                4095

Leu Thr Ser Leu Ser Ser Val Ser Thr Gly Asp Thr Thr Pro Leu
4100                4105                4110

Pro Val Thr Asp Thr Ser Ser Ala Ser Thr Gly Gln Ala Thr Pro
4115                4120                4125

Leu Pro Val Thr Ser Leu Ser Ser Val Ser Thr Gly Asp Thr Thr
4130                4135                4140

Pro Leu Pro Val Thr Ile Pro Ser Ser Ala Ser Ser Gly His Thr
4145                4150                4155

Thr Ser Leu Pro Val Thr Asp Ala Ser Ser Val Ser Thr Gly His
4160                4165                4170

Gly Thr Pro Leu Pro Val Thr Ser Thr Ser Ser Ala Ser Thr Gly
4175                4180                4185

Asp Thr Thr Pro Leu Pro Val Thr Asp Thr Ser Ser Ala Ser Thr
4190                4195                4200

Gly His Ala Thr Pro Leu Pro Val Thr Asp Thr Ser Ser Ala Ser
4205                4210                4215

Thr Gly His Ala Thr Pro Leu Pro Val Thr Ser Leu Ser Ser Val
4220                4225                4230
```

```
Ser Thr Gly His Ala Thr Pro Leu Ala Val Ser Ser Ala Thr Ser
    4235             4240                4245
Ala Ser Thr Val Ser Ser Asp Ser Pro Leu Lys Met Glu Thr Pro
    4250             4255                4260
Gly Met Thr Thr Pro Ser Leu Lys Thr Asp Gly Gly Arg Arg Thr
    4265             4270                4275
Ala Thr Ser Pro Pro Pro Thr Thr Ser Gln Thr Ile Ile Ser Thr
    4280             4285                4290
Ile Pro Ser Thr Ala Met His Thr Arg Ser Thr Ala Ala Pro Ile
    4295             4300                4305
Pro Ile Leu Pro Glu Arg Gly Val Ser Leu Phe Pro Tyr Gly Ala
    4310             4315                4320
Gly Ala Gly Asp Leu Glu Phe Val Arg Arg Thr Val Asp Phe Thr
    4325             4330                4335
Ser Pro Leu Phe Lys Pro Ala Thr Gly Phe Pro Leu Gly Ser Ser
    4340             4345                4350
Leu Arg Asp Ser Leu Tyr Phe Thr Asp Asn Gly Gln Ile Ile Phe
    4355             4360                4365
Pro Glu Ser Asp Tyr Gln Ile Phe Ser Tyr Pro Asn Pro Leu Pro
    4370             4375                4380
Thr Gly Phe Thr Gly Arg Asp Pro Val Ala Leu Val Ala Pro Phe
    4385             4390                4395
Trp Asp Asp Ala Asp Phe Ser Thr Gly Arg Gly Thr Thr Phe Tyr
    4400             4405                4410
Gln Glu Tyr Glu Thr Phe Tyr Gly Glu His Ser Leu Leu Val Gln
    4415             4420                4425
Gln Ala Glu Ser Trp Ile Arg Lys Met Thr Asn Asn Gly Gly Tyr
    4430             4435                4440
Lys Ala Arg Trp Ala Leu Lys Val Thr Trp Val Asn Ala His Ala
    4445             4450                4455
Tyr Pro Ala Gln Trp Thr Leu Gly Ser Asn Thr Tyr Gln Ala Ile
    4460             4465                4470
Leu Ser Thr Asp Gly Ser Arg Ser Tyr Ala Leu Phe Leu Tyr Gln
    4475             4480                4485
Ser Gly Gly Met Gln Trp Asp Val Ala Gln Arg Ser Gly Asn Pro
    4490             4495                4500
Val Leu Met Gly Phe Ser Ser Gly Asp Gly Tyr Phe Glu Asn Ser
    4505             4510                4515
Pro Leu Met Ser Gln Pro Val Trp Glu Arg Tyr Arg Pro Asp Arg
    4520             4525                4530
Phe Leu Asn Ser Asn Ser Gly Leu Gln Gly Leu Gln Phe Tyr Arg
    4535             4540                4545
Leu His Arg Glu Glu Arg Pro Asn Tyr Arg Leu Glu Cys Leu Gln
    4550             4555                4560
Trp Leu Lys Ser Gln Pro Arg Trp Pro Ser Trp Gly Trp Asn Gln
    4565             4570                4575
Val Ser Cys Pro Cys Ser Trp Gln Gln Gly Arg Arg Asp Leu Arg
    4580             4585                4590
Phe Gln Pro Val Ser Ile Gly Arg Trp Gly Leu Gly Ser Arg Gln
    4595             4600                4605
Leu Cys Ser Phe Thr Ser Trp Arg Gly Gly Val Cys Cys Ser Tyr
    4610             4615                4620
```

-continued

Gly Pro Trp Gly Glu Phe Arg Glu Gly Trp His Val Gln Arg Pro
4625                4630                4635

Trp Gln Leu Ala Gln Glu Leu Glu Pro Gln Ser Trp Cys Cys Arg
    4640                4645                4650

Trp Asn Asp Lys Pro Tyr Leu Cys Ala Leu Tyr Gln Gln Arg Arg
    4655                4660                4665

Pro His Val Gly Cys Ala Thr Tyr Arg Pro Pro Gln Pro Ala Trp
    4670                4675                4680

Met Phe Gly Asp Pro His Ile Thr Thr Leu Asp Gly Val Ser Tyr
    4685                4690                4695

Thr Phe Asn Gly Leu Gly Asp Phe Leu Leu Val Gly Ala Gln Asp
    4700                4705                4710

Gly Asn Ser Ser Phe Leu Leu Gln Gly Arg Thr Ala Gln Thr Gly
    4715                4720                4725

Ser Ala Gln Ala Thr Asn Phe Ile Ala Phe Ala Ala Gln Tyr Arg
    4730                4735                4740

Ser Ser Ser Leu Gly Pro Val Thr Val Gln Trp Leu Leu Glu Pro
    4745                4750                4755

His Asp Ala Ile Arg Val Leu Leu Asp Asn Gln Thr Val Thr Phe
    4760                4765                4770

Gln Pro Asp His Glu Asp Gly Gly Gln Glu Thr Phe Asn Ala
    4775                4780                4785

Thr Gly Val Leu Leu Ser Arg Asn Gly Ser Glu Val Ser Ala Ser
    4790                4795                4800

Phe Asp Gly Trp Ala Thr Val Ser Val Ile Ala Leu Ser Asn Ile
    4805                4810                4815

Leu His Ala Ser Ala Ser Leu Pro Pro Glu Tyr Gln Asn Arg Thr
    4820                4825                4830

Glu Gly Leu Leu Gly Val Trp Asn Asn Asn Pro Glu Asp Asp Phe
    4835                4840                4845

Arg Met Pro Asn Gly Ser Thr Ile Pro Pro Gly Ser Pro Glu Glu
    4850                4855                4860

Met Leu Phe His Phe Gly Met Thr Trp Gln Ile Asn Gly Thr Gly
    4865                4870                4875

Leu Leu Gly Lys Arg Asn Asp Gln Leu Pro Ser Asn Phe Thr Pro
    4880                4885                4890

Val Phe Tyr Ser Gln Leu Gln Lys Asn Ser Ser Trp Ala Glu His
    4895                4900                4905

Leu Ile Ser Asn Cys Asp Gly Asp Ser Ser Cys Ile Tyr Asp Thr
    4910                4915                4920

Leu Ala Leu Arg Asn Ala Ser Ile Gly Leu His Thr Arg Glu Val
    4925                4930                4935

Ser Lys Asn Tyr Glu Gln Ala Asn Ala Thr Leu Asn Gln Tyr Pro
    4940                4945                4950

Pro Ser Ile Asn Gly Gly Arg Val Ile Glu Ala Tyr Lys Gly Gln
    4955                4960                4965

Thr Thr Leu Ile Gln Tyr Thr Ser Asn Ala Glu Asp Ala Asn Phe
    4970                4975                4980

Thr Leu Arg Asp Ser Cys Thr Asp Leu Glu Leu Phe Glu Asn Gly
    4985                4990                4995

Thr Leu Leu Trp Thr Pro Lys Ser Leu Glu Pro Phe Thr Leu Glu
    5000                5005                5010

```
Ile Leu Ala Arg Ser Ala Lys Ile Gly Leu Ala Ser Ala Leu Gln
5015                5020                5025

Pro Arg Thr Val Val Cys His Cys Asn Ala Glu Ser Gln Cys Leu
5030                5035                5040

Tyr Asn Gln Thr Ser Arg Val Gly Asn Ser Ser Leu Glu Val Ala
5045                5050                5055

Gly Cys Lys Cys Asp Gly Gly Thr Phe Gly Arg Tyr Cys Glu Gly
5060                5065                5070

Ser Glu Asp Ala Cys Glu Glu Pro Cys Phe Pro Ser Val His Cys
5075                5080                5085

Val Pro Gly Lys Gly Cys Glu Ala Cys Pro Pro Asn Leu Thr Gly
5090                5095                5100

Asp Gly Arg His Cys Ala Ala Leu Gly Ser Ser Phe Leu Cys Gln
5105                5110                5115

Asn Gln Ser Cys Pro Val Asn Tyr Cys Tyr Asn Gln Gly His Cys
5120                5125                5130

Tyr Ile Ser Gln Thr Leu Gly Cys Gln Pro Met Cys Thr Cys Pro
5135                5140                5145

Pro Ala Phe Thr Asp Ser Arg Cys Phe Leu Ala Gly Asn Asn Phe
5150                5155                5160

Ser Pro Thr Val Asn Leu Glu Leu Pro Leu Arg Val Ile Gln Leu
5165                5170                5175

Leu Leu Ser Glu Glu Glu Asn Ala Ser Met Ala Glu Val Asn Ala
5180                5185                5190

Ser Val Ala Tyr Arg Leu Gly Thr Leu Asp Met Arg Ala Phe Leu
5195                5200                5205

Arg Asn Ser Gln Val Glu Arg Ile Asp Ser Ala Ala Pro Ala Ser
5210                5215                5220

Gly Ser Pro Ile Gln His Trp Met Val Ile Ser Glu Phe Gln Tyr
5225                5230                5235

Arg Pro Arg Gly Pro Val Ile Asp Phe Leu Asn Asn Gln Leu Leu
5240                5245                5250

Ala Ala Val Val Glu Ala Phe Leu Tyr His Val Pro Arg Arg Ser
5255                5260                5265

Glu Glu Pro Arg Asn Asp Val Val Phe Gln Pro Ile Ser Gly Glu
5270                5275                5280

Asp Val Arg Asp Val Thr Ala Leu Asn Val Ser Thr Leu Lys Ala
5285                5290                5295

Tyr Phe Arg Cys Asp Gly Tyr Lys Gly Tyr Asp Leu Val Tyr Ser
5300                5305                5310

Pro Gln Ser Gly Phe Thr Cys Val Ser Pro Cys Ser Arg Gly Tyr
5315                5320                5325

Cys Asp His Gly Gly Gln Cys Gln His Leu Pro Ser Gly Pro Arg
5330                5335                5340

Cys Ser Cys Val Ser Phe Ser Ile Tyr Thr Ala Trp Gly Glu His
5345                5350                5355

Cys Glu His Leu Ser Met Lys Leu Asp Ala Phe Phe Gly Ile Phe
5360                5365                5370

Phe Gly Ala Leu Gly Gly Leu Leu Leu Leu Gly Val Gly Thr Phe
5375                5380                5385
```

-continued

```
Val Val Leu Arg Phe Trp Gly Cys Ser Gly Ala Arg Phe Ser Tyr
    5390                5395                5400

Phe Leu Asn Ser Ala Glu Ala Leu Pro
    5405                5410
```